US011331009B2

(12) United States Patent
Ionescu et al.

(10) Patent No.: US 11,331,009 B2
(45) Date of Patent: May 17, 2022

(54) APPARATUS FOR NON-INVASIVE SENSING OF BIOMARKERS IN HUMAN SWEAT

(71) Applicants: Xsensio SA, Lausanne (CH); ECOLE POLYTECHNIQUE FEDERALE DE LAUSANNE (EPFL), Lausanne (CH)

(72) Inventors: Mihai Adrian Ionescu, Ecublens (CH); Johan Frédéric Longo, Yverdon-les-Bains (CH); Fabien Patrick Wildhaber, Troistorrents (CH); Hoël Maxime Guérin, Lausanne (CH); Francesco Bellando, Renens (CH); Erick García Cordero, Lausanne (CH)

(73) Assignees: Xsensio SA, Lausanne (CH); ECOLE POLYTECHNIQUE FEDERALE DE LAUSANNE (EPFL), Lausanne (CH)

( * ) Notice: Subject to any disclaimer, the term of this patent is extended or adjusted under 35 U.S.C. 154(b) by 420 days.

(21) Appl. No.: 15/913,714

(22) Filed: Mar. 6, 2018

(65) Prior Publication Data
US 2019/0110722 A1 Apr. 18, 2019

Related U.S. Application Data

(60) Provisional application No. 62/573,637, filed on Oct. 17, 2017, provisional application No. 62/573,124, filed on Oct. 16, 2017.

(51) Int. Cl.
*A61B 5/145* (2006.01)
*B01L 3/00* (2006.01)
(Continued)

(52) U.S. Cl.
CPC ........ *A61B 5/14517* (2013.01); *A61B 5/0004* (2013.01); *A61B 5/0022* (2013.01);
(Continued)

(58) Field of Classification Search
None
See application file for complete search history.

(56) References Cited

U.S. PATENT DOCUMENTS 6,616,823 B2 * 9/2003 Kopf-Sill .......... B01L 3/502746
204/602
9,116,145 B2 * 8/2015 Li .................... B01L 3/502707
(Continued)

FOREIGN PATENT DOCUMENTS

EP 3629901 A1 4/2020
WO WO-2010/045247 A1 4/2010
(Continued)

OTHER PUBLICATIONS

Song, H. and Ismagilov, R. F., Millisecond Kinetics on a Microfluidic Chip Using Nanoliters of Reagents, Journal of the American Chemical Society, 125(47):14613-14619 (2003).
(Continued)

*Primary Examiner* — Marjan Fardanesh
(74) *Attorney, Agent, or Firm* — Choate, Hall & Stewart LLP; William R. Haulbrook; Michael D. Schmitt

(57) ABSTRACT

Presented herein are devices for collecting and/or channeling a biofluid (e.g., sweat, tears, saliva) and detecting and/or quantifying one or more biomarkers in the biofluid. The one or more biomarkers may include, for example, ions, salts thereof, hormones and/or steroids, proteins, metabolites and organic compounds. In certain embodiments, the devices described herein include a specially designed interface and a zero-energy micro pump that allow the device to be comfortably affixed directly to the skin of a user while biofluid is efficiently and non-invasively collected from the skin of the user. In certain embodiments, the biofluid collection and sensing device is housed on or in another wearable device, such as a wrist band or a smart watch. In certain embodiments, the devices described herein are dis-
(Continued)

posable (e.g., after a certain period of use and/or wear the device can be disposed and replaced with a low-cost replacement).

25 Claims, 27 Drawing Sheets

(51) Int. Cl.
| | |
|---|---|
| G01N 33/487 | (2006.01) |
| A61B 5/1486 | (2006.01) |
| A61B 5/00 | (2006.01) |
| A61B 10/00 | (2006.01) |
| G01N 27/07 | (2006.01) |
| A61B 5/1477 | (2006.01) |

(52) U.S. Cl.
CPC .......... *A61B 5/1477* (2013.01); *A61B 5/1486* (2013.01); *A61B 5/14539* (2013.01); *A61B 5/14546* (2013.01); *A61B 5/4266* (2013.01); *A61B 5/6833* (2013.01); *A61B 10/0064* (2013.01); *B01L 3/50273* (2013.01); *B01L 3/502715* (2013.01); *G01N 27/07* (2013.01); *G01N 33/48707* (2013.01); *G01N 33/48792* (2013.01); *A61B 5/0002* (2013.01); *A61B 5/681* (2013.01); *A61B 2503/10* (2013.01); *A61B 2560/0412* (2013.01); *A61B 2562/028* (2013.01); *A61B 2562/0285* (2013.01); *B01L 2300/023* (2013.01); *B01L 2300/0645* (2013.01); *B01L 2300/0861* (2013.01); *B01L 2400/04* (2013.01); *B01L 2400/0406* (2013.01)

(56) References Cited

U.S. PATENT DOCUMENTS

| | | | |
|---|---|---|---|
| 9,570,288 B2 | 2/2017 | Rigante et al. | |
| 9,810,660 B2* | 11/2017 | Hu | H01L 27/1211 |
| 10,653,342 B2 | 5/2020 | Rogers et al. | |
| 10,736,551 B2 | 8/2020 | Rogers | |
| 10,925,523 B2 | 2/2021 | Rogers et al. | |
| 2002/0049389 A1* | 4/2002 | Abreu | A61B 5/412 600/558 |
| 2004/0129678 A1* | 7/2004 | Crowley | B01D 61/18 216/84 |
| 2004/0150029 A1 | 8/2004 | Lee | |
| 2005/0106713 A1 | 5/2005 | Phan et al. | |
| 2005/0241959 A1 | 11/2005 | Ward et al. | |
| 2005/0250279 A1 | 11/2005 | Son et al. | |
| 2007/0027383 A1 | 2/2007 | Peyser et al. | |
| 2009/0278196 A1 | 11/2009 | Chang et al. | |
| 2010/0141280 A1 | 6/2010 | Yang et al. | |
| 2011/0034912 A1 | 2/2011 | de Graff et al. | |
| 2011/0049599 A1 | 3/2011 | Taketani | |
| 2014/0134748 A1 | 5/2014 | Liu et al. | |
| 2015/0021690 A1 | 1/2015 | Jacob et al. | |
| 2015/0268189 A1 | 9/2015 | Rigante et al. | |
| 2015/0372119 A1 | 12/2015 | Zhang et al. | |
| 2016/0310049 A1 | 10/2016 | Rowe et al. | |
| 2017/0023157 A1 | 1/2017 | Hayes | |
| 2017/0100102 A1 | 4/2017 | Heikenfeld | |
| 2017/0231571 A1 | 8/2017 | Rogers et al. | |
| 2018/0020966 A1 | 1/2018 | Begtrup et al. | |
| 2018/0064377 A1* | 3/2018 | Rogers | G01N 33/50 |
| 2018/0153451 A1 | 6/2018 | Heikenfeld et al. | |
| 2018/0195999 A1 | 7/2018 | Liu et al. | |
| 2018/0199866 A1 | 7/2018 | Heikenfeld | |
| 2018/0263539 A1 | 9/2018 | Javey et al. | |
| 2018/0340903 A1 | 11/2018 | Heikenfeld | |
| 2019/0117170 A1 | 4/2019 | Begtrup et al. | |
| 2019/0183398 A1 | 6/2019 | Heikenfeld et al. | |
| 2019/0191998 A1 | 6/2019 | Heikenfeld et al. | |
| 2019/0191999 A1 | 6/2019 | Heikenfeld et al. | |
| 2019/0192000 A1 | 6/2019 | Heikenfeld et al. | |
| 2019/0254641 A1 | 8/2019 | Begtrup et al. | |
| 2019/0307372 A1 | 10/2019 | Ocampo et al. | |
| 2020/0077988 A1 | 3/2020 | Heikenfeld | |
| 2020/0315503 A1 | 10/2020 | Heikenfeld et al. | |
| 2020/0397352 A1 | 12/2020 | Wildhaber et al. | |

FOREIGN PATENT DOCUMENTS

| | | |
|---|---|---|
| WO | WO-2012/050873 A2 | 4/2012 |
| WO | WO-2016/030869 A1 | 3/2016 |
| WO | WO-201 7/019573 A1 | 2/2017 |
| WO | WO-2018/047125 A1 | 3/2018 |
| WO | WO-2018/223090 A1 | 12/2018 |
| WO | WO-2019/060689 A1 | 3/2019 |
| WO | WO-2019/170776 A1 | 9/2019 |
| WO | WO-2020/106353 A1 | 5/2020 |
| WO | WO-2021/099610 A1 | 5/2021 |

OTHER PUBLICATIONS

International Search Report, International Application No. PCT/EP2018/077793 (Apparatus for Non-Invasive Sensing of Biomarkers in Human Sweat, filed Oct. 11, 2018), issued by ISA/European Patent Office, 6 pages, dated Jun. 28, 2019.

Written Opinion, International Application No. PCT/EP2018/077793 (Apparatus for Non-Invasive Sensing of Biomarkers in Human Sweat, filed Oct. 11, 2018), issued by ISA/European Patent Office, 11 pages, dated Jun. 28, 2019.

Morse, J. et al., Wearable Microfluidic Biomarker Sensor for Human Performance Assessment, 6th Electronic System-Integration Technology Conference, IEEE, pp. 1-3, (2016).

Partial International Search Report and Accompanying Provisional Written Opinion, International Application No. PCT/EP2018/077793 (Apparatus for Non-Invasive Sensing of Biomarkers in Human Sweat, filed Oct. 11, 2018), issued by ISA/European Patent Office, 10 pages, dated May 3, 2019.

Aliakbarinodehi, N. et al., Aptamer-based Field-Effect Biosensor for Tenofovir Detection, Scientific Reports, 7:1-10, Article No. 44409, Mar. 15, 2017.

Bellando, F., Lab OnSkin™: 3D Monolithically Integrated Zero-Energy Micro/Nanofludics and FD SOI Ion Sensitive FETs for Wearable Multi-Sensing Sweat Applications, IEEE, IEDM17-437, 18.1.1-18.1.4, (Dec. 2017).

Cho, E. et al., A Seif-Powered Sensor Patch for Glucose Monitoring in Sweat, IEEE MEMS Conf. 2017, pp. 366-369, (Jan. 2017).

Craighead, H., Future lab-on-a-chip technologies for interrogating individual molecules, Nature, (Jul. 27, 2006), 442:387-393, (2006).

Dieffenderfer, J. et al., Towards a Sweat-based Wireless and Wearable Electrochemical Sensor, IEEE Sensors, 978-1-4799-8287, 3 pages, (2016).

Gao, W. et al., A. Javey, Fully integrated wearable sensor arrays for multiplexed in situ perspiration analysis, Nature, 529(7587):509-514, (2016).

Gao, W. et al., Wearable Sweat Biosensors, IEEE, IEDM16:161-164 (2016).

Garcia-Cordero, E. et al., Heterogeneous integration of low power pH FinFet sensors with passive capillary microfluidics and miniaturized Ag/AgCI quasi-Reference Electrode, 2016 46th European Solid-State Device Research Conference, IEEE, pp. 452-455 (2016).

Heikenfeld, J., Non-invasive Analyte Access and Sensing through Eccrine Sweat: Challenges and Outlook circa, , 28(6):1242-1249, (2016).

Hideshima, S. et al., Attomolar detection of influenza A virus hemagglutinin human H1 and avian H5 using glycan-blotted field effect transistor biosensor, 2013.

International Search Report, PCT/IB2017/055456, 5 pages, dated Nov. 15, 2017.

Iskierko, Z. et al., Extended-gate field-effect transistor (EG-FET) with molecularly imprinted polymer (MIP) film for selective inosine determination, Biosensors and Bioelectronics, 4(15):526-533, (2015).

Kim, D. et al., Epidermal Electronics, Science, 333:838-843, (2011).

(56) References Cited

OTHER PUBLICATIONS

Kim, D. et al., Graphene-based wearable electronic patch for diabetes control, SPIE Newsroom, 3 pages, (2016).

Kinnamon, D. et al., Electronic Bracelet for Monitoring of Alcohol Lifestyle, IEEE Sensors, 2016, pp. 1-3.

Livi, P. et al., A Hybrid FinFET-based Biosensor with Integrated Readout Capability, Procedia Engineering, 47:821-824 (2012).

Morak; Jurgen et al., Design and evaluation of a telemonitoring concept based on NFC-enabled mobile phones and sensor devices, IEEE transactions on information technology in biomedicine, (20120000), 16.1:17-23.

Rigante, S. et al., Sensing with Advanced Computing Technology: Fin Field-Effect Transistors with High-k Gate Stack on Bulk Silicon, ACS NANO 9(5):4872-4881 (2015).

Rose, D. P. et al., Adhesive RFID Sensor Patch for Monitoring of Sweat Electrolytes, IEEE Transactions on Biomedical Engineering, 62(6):1457-1465 (2015).

Safavieh, R. et al., Capillaries: pre-programmed, self-powered microfluidic circuits built form capillary elements, Lab on a Chip, 12(21):4180-4189 (2013).

Trenz, F. et al., Evaluation of a reflection based dehydration sensing method for wristwatch integration, Microwave, Radar and Wireless Communications, (MIKON), 21st International Conference on IEEE, (2016).

Vericat, C. et al., Self-assembled monolayers of thiolates on metals: a review article on sulfur-metal chemistry and surface structures, RSC Advances, 4:27730-27754, (2014).

Widayani, et al., Preliminary Study of Molecularly Imprinted Polymer-based Potentiometric Sensor for Glucose, Science Direct, Procedia Engineering, 170:84-87, (2017).

Written Opinion, PCT/IB2017/055456, 5 pages, dated Nov. 15, 2017.

Zimmermann, M. et al., Capillary pumps for autonomous capillary systems, Lab on a Chip, 7(1):119 (2007).

International Search Report, Application No. PCT/EP2015/055616 (System for Collection and Analysis of Biofluid From Skin and Method of Using the Same, filed Mar. 6, 2019), issued by ISA/European Patent Office, 4 pages, dated May 16, 2019.

Written Opinion, International Application No. PCT/EP2015/055616 (System for Collection and Analysis of Biofluid From Skin and Method of Using the Same, filed Mar. 6, 2019), issued by ISA/European Patent Office, 8 pages, dated May 16, 2019.

\* cited by examiner

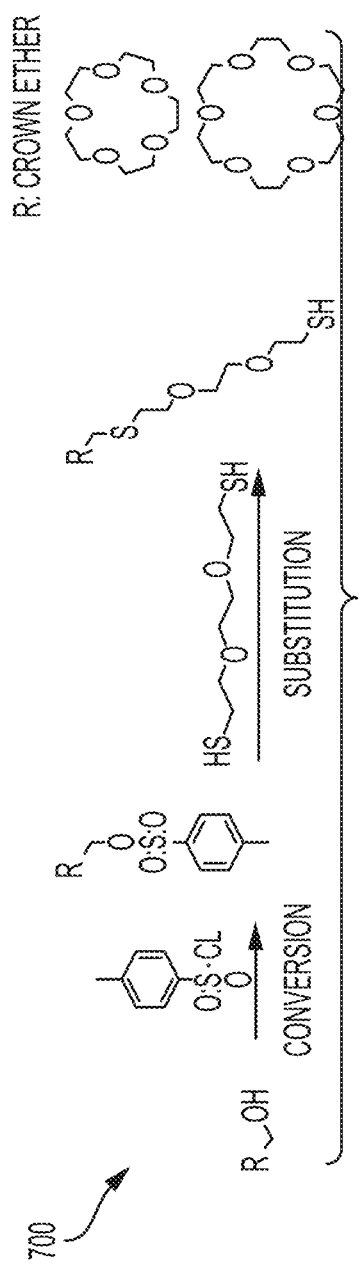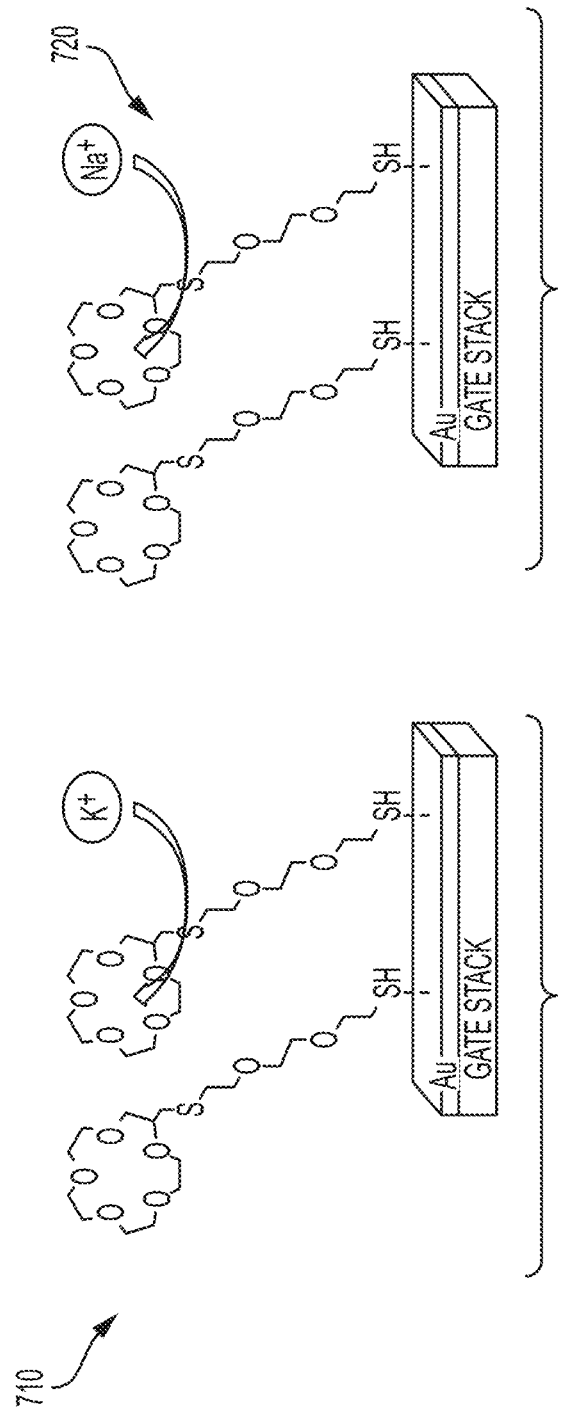
FIG. 7A
FIG. 7B
FIG. 7C

APPARATUS FOR NON-INVASIVE SENSING OF BIOMARKERS IN HUMAN SWEAT

PRIORITY APPLICATIONS

This application claims priority to and the benefit of U.S. Provisional Patent Application No. 62/573,637, filed on Oct. 17, 2017, and U.S. Provisional Patent Application No. 62/573,124 filed on Oct. 16, 2017, the contents of which are hereby incorporated by reference herein in their entirety.

FIELD OF THE INVENTION

This invention relates generally to an apparatus for detection of biomarkers in bio-fluids (e.g., human sweat, tears, saliva). In certain embodiments, the invention relates to skin patches and other wearable devices comprising a biofluid detection and sensing device for in situ, continuous, non-invasive sensing of biomarkers (e.g., proteins, hormones, ions) in biofluids.

BACKGROUND OF THE INVENTION

A biomarker is a measurable substance in an organism. The presence and/or quantity of a biomarker in a biofluid of the organism is indicative of some phenomenon and/or characteristic of the organism such as a disease, an infection, an environmental exposure (e.g., to a chemical), or state of being (e.g., a level of stress). Examples of commonly measured biomarkers in humans include proteins, hormones, metabolites, and ions. For example, glucose is a biomarker that is typically measured in the blood of diabetic individuals to help them manage their disease.

Biomarkers are often measured in blood. Acquiring blood samples is invasive and can cause significant discomfort to the individual's being tested. Typical strategies of biomarker analysis involve obtaining a blood sample from a person and performing a test (e.g., for biomarker detection and/or quantification) in a laboratory. This process is slow, expensive, and limited to a single sampling moment in time. Using existing techniques, each blood sample that is obtained often must be stored and transported to an appropriate laboratory where biomarker analysis can be performed by specially trained technicians using specialized equipment. This sequence of steps adds to the cost (e.g., of laboratory equipment and technician time) and time (e.g., for transport and manual analysis) required for biomarker analysis. Biomarker analysis, from the time of sample collection to the time results reach an individual being tested (e.g., a patient), commonly takes hours, days, or longer before results are available.

Since existing technology for measuring biomarkers only provides biomarker analysis data at discrete time points, biomarkers cannot be effectively measured continuously or in real-time. If frequent biomarker measurements are needed (e.g., several measurements per hour), many blood samples must be acquired from the individual being tested, leading to a significant increase in discomfort and inconvenience.

There is thus a need for improved systems and methods for continuous, non-invasive detection and/or quantification of biomarkers in biofluids.

SUMMARY OF THE INVENTION

Presented herein are devices for collecting and/or channeling a biofluid (e.g., sweat, tears, saliva) and detecting and/or quantifying one or more biomarkers in the biofluid. The one or more biomarkers may include, for example, ions, salts thereof, hormones and/or steroids, proteins, metabolites and organic compounds. In certain embodiments, the devices described herein include a specially designed interface and a zero-energy micro pump that allow the device to be comfortably affixed directly to the skin of a user while biofluid is efficiently and non-invasively collected from the skin of the user. In certain embodiments, the biofluid collection and sensing device is housed on or in another wearable device, such as a wrist band or a smart watch. In certain embodiments, the devices described herein are disposable (e.g., after a certain period of use and/or wear the device can be disposed and replaced with a low-cost replacement).

The biofluid collection and sensing devices described herein can be used to acquire, record, and analyze information about the health, wellness, and/or other conditions of a wearer of the device in a substantially real-time (e.g., continuous) manner. For example, an athlete may wear an embodiment of the devices described herein to monitor biomarkers levels in real-time during training. The biofluid collection and sensing device may be housed in a smart watch such that the athlete, after a training session, can review a record of their electrolyte and lactate levels during the session. Analysis of this data can be used to improve future athletic performance.

The biofluid collection and sensing devices described herein provide for faster and lower cost biomarker sensing than is possible using previous technology. In certain embodiments, the biofluid collection and sensing device described herein includes a specially designed fully depleted field effect transistor (FD-FET) sensor. This sensor has a ribbon-like geometry, which when used as an FD-FET, allows for devices with less complex fabrication processes, improved electrostatic control, decreased parasitic capacitance between source and drain, decreased leakage currents, and decreased power consumption compared to previous technologies. These features work in synergy to provide improved sensitivity and specificity of high frequency measurements. The biofluid collection and sensing devices described herein can allow for more rapid and lower cost detection of a biomarker associated with a disease, allowing earlier diagnosis of the disease and earlier administration of an appropriate therapy.

In certain embodiments, the biofluid collection and sensing device is used in clinical trial monitoring. For example, each participant in a clinical trial may wear a biofluid collection and sensing device to continuously monitor biomarker levels throughout the course of a longitudinal clinical trial. Participants may thus not be required to go into the clinic for conventional biomarker measurements, making participation easier. The biofluid collection and sensing device can also be configured to acquire biomarker analysis data at a higher frequency during times of increased interest for the study. For example, biomarkers may be sensed more frequently just before and after administration of a pharmaceutical agent being tested in the clinical trial. This fine-grained biomarker data is not possible using previous technology.

In certain embodiments, the biofluid collection and sensing device is or is part of a biofluid collection and sensing wearable device for on-the-body use and on-body biofluid sensing. In certain embodiments, the plurality of semiconductor sensors extends in a first plane, and the at least one reference electrode extends in a second plane above said first plane.

In one aspect, the present disclosure is directed to a biofluid (e.g., sweat, e.g., human sweat) collection and sensing device (e.g., wearable device). The device comprises an interface (e.g., a substrate) and/or interface surface comprising at least one biocompatible material for contacting a body part (e.g., skin); at least one inlet for receiving a biofluid (e.g., wherein the biofluid naturally emanates from a wearer of the device); at least one outlet for evacuating the biofluid (e.g., out of the device); a plurality of semiconductor sensors for detecting (e.g. detecting the presence of and/or quantifying) one or more biomarkers in the received biofluid; and at least one microfluidic and/or nanofluidic channel in fluid communication with the at least one inlet, at least one sensor of the plurality of semiconductor sensors, and at least one outlet (e.g., and, optionally, at least one reference electrode) (e.g., wherein the at least one microfluidic and/or nanofluidic channel houses and/or runs across and/or intersects with and/or guides the bio-fluid such that the bio-fluid comes into contact with, the plurality of semiconductor sensors).

In certain embodiments, the biofluid collection and sensing device comprises at least one reference electrode for biasing a gate of at least one of the semiconductor sensors (e.g., wherein the at least one reference electrode is fully embedded inside the device, e.g., wherein the at least one reference electrode comprises Ag/AgCl, e.g., wherein the at least one reference electrode comprises a miniaturized Ag/AgCl quasi-reference electrode (QRE)). In certain embodiments, the reference electrode is a quasi-reference electrode (QRE), wherein the QRE is a film comprising silver and silver chloride (e.g., wherein the QRE comprises Ag/AgCl) (e.g., wherein the film has a thickness of 500 μm or less) [e.g., wherein the QRE comprises a protective membrane (e.g., a polyvinyl butyral (PVB) or Nafion® membrane loaded with NaCl or other chloride-containing salt) (e.g., wherein the protective membrane has a thickness of 100 μm or less)].

In certain embodiments, the one or more biomarkers include one or more members selected from the group consisting of ions (e.g., chloride, sodium, potassium, calcium, ammonium, silver ions, and chromium ions), hormones and/or steroids (e.g., steroid hormones, dehydroepiandrosterone (DHEA), estrogen, vasopressin, cholesterol, adrenalin, cortisol, and cortisone), proteins (e.g., cytokines, CFP, ESAT-10 (a tuberculosis biomarker), and neuropeptides), metabolites (e.g., alcohol, lactic acid, lactate, urea, and creatinine), and organic compounds [e.g., vitamins (e.g., ascorbic acid), glucose, penicillin, and hydrogen peroxide)].

In certain embodiments, the plurality of semiconductor sensors comprise one or more arrays of field effect transistors (FETs) [e.g., ion-sensitive fully depleted (FD)ISFETs, e.g., wherein the one or more arrays of FETs comprise liquid gates (e.g., wherein each of the liquid gates is functionalized for detection of selected electrolytes), e.g., wherein a gate of at least one of the plurality of semiconductor sensors comprises hafnium dioxide ($HfO_2$)] (e.g., wherein the plurality of semiconductor sensors are CMOS-compatible). In certain embodiments, the one or more arrays of field effect transistors (FETs) comprise at least one fully depleted FET (FD-FET) (e.g., wherein the FD-FET has a ribbon-like geometry) (e.g., wherein a surface area of a gate of the FD-FET is in a range from about 1 μm$^2$ to about 1000 μm$^2$, e.g., wherein a surface area of a gate of the FD-FET is in a range from about 35 μm$^2$ to about 150 μm$^2$).

In certain embodiments, the plurality of semiconductor sensors comprise functionalized gates, wherein the functionalized gates comprise a selective moiety (e.g., a crown ether), aptamers, antibodies, or enzymes for the selective detection of a biomarker of interest (e.g., sodium ion, e.g., potassium ion) (e.g., wherein the functionalized gates are configured to detect a plurality of different biomarkers in the received bio-fluid).

In certain embodiments, the plurality of semiconductor sensors are disposed on a first semiconductor or semiconductor-on-insulator (SOI) (e.g., FD-SOI) substrate layer; the at least one microfluidic or nanofluidic channel is formed from a second substrate layer (e.g., wherein the second substrate layer comprises two or more integrated microfluidic layers); and the first and second substrates are connected one to the other to form the (integrated) biofluid collection and sensing device (e.g., wherein the first substrate houses and/or supports at least one reference electrode embedded therein or disposed thereupon to contact the biofluid).

In certain embodiments, the plurality of semiconductor sensors and the at least one microfluidic or nanofluidic channel are disposed on a first semiconductor or semiconductor-on-insulator (SOI) (e.g., FD-SOI) substrate layer.

In certain embodiments, the biofluid collection and sensing device comprises one or more microfluidic layers [e.g., two or more integrated microfluidic layers disposed upon a layer comprising the plurality of semiconductor sensors, e.g., said two or more integrated microfluidic layers providing the at least one microfluidic and/or nanofluidic channel capable of collecting and conducting the biofluid (e.g., sweat) to the plurality of semiconductor sensors via capillary forces (e.g., via zero-energy biofluid pumping)].

In certain embodiments, the one or more microfluidic layers are biocompatible [e.g., wherein the one or more microfluidic layers comprise glass, silicon, aluminum oxide, silicon dioxide, an oxide, a resin, a photoresist, a pressure sensitive adhesive (PSA), SU-8

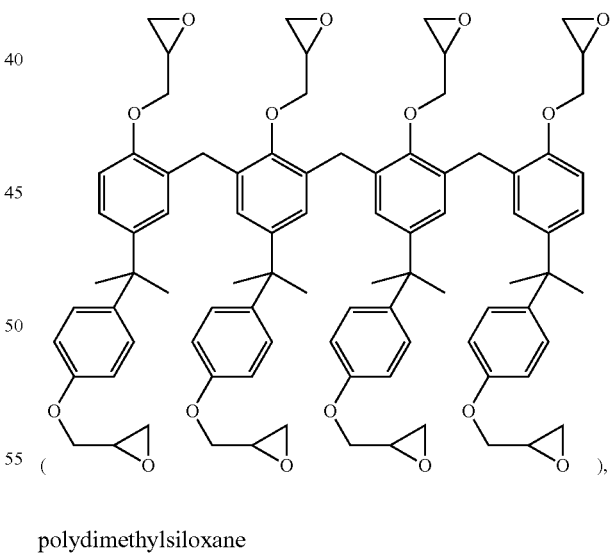

polydimethylsiloxane

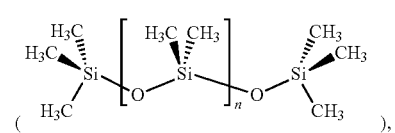

and polycarbonate

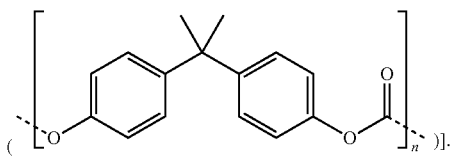

In certain embodiments, the at least one microfluidic and/or nanofluidic channel is shaped and sized to transfer the bio-fluid from the at least one inlet, through the at least one microfluidic and/or nanofluidic channel, and out of the at least one outlet via capillary motion (e.g. solely via capillary motion, e.g., zero-energy) (e.g., wherein at least a portion of at least one of the microfluidic or nanofluidic channel has a serpentine shape, e.g., which directs the bio-fluid flowing therethrough over/around/through/by one or more of the plurality of semiconductor sensors).

In certain embodiments, the at least one microfluidic or nanofluidic channel has an internal volume from about 0.1 nL to about 100 nL (e.g., wherein the at least one microfluidic and/or nanofluidic channel has a width in a range from about 100 nm to about 1000 μm and a height in a range from about 100 nm to about 500 μm, e.g., wherein a portion the at least one microfluidic and/or nanofluidic channel has a height of about 100 nm or less).

In certain embodiments, the biofluid collection and sensing device comprises at least one micro pump for controlling fluid flow (e.g., at a substantially constant flow rate) (e.g., wherein the micro pump is a zero-energy microfluidic pump structure whose size and shape controls fluid flow, e.g., via capillary motion). In certain embodiments, each of the at least one micro pump comprises a plurality (e.g., an array) of micro-pillars (e.g., the array of micro-pillars having an arrangement in the at least one micro pump to establish and/or facilitate fluid flow). In certain embodiments, the at least one micro pump provides a substantially constant flow rate of the biofluid (e.g., a sub-nanoliter/minute flow rate) (e.g., wherein the flow rate has a value from about 1 pL/minute to about 5 nL/minute, e.g., from about 10 pL/minute to about 3 nL/minute, e.g., from about 50 pL/minute to about 1000 pL/minute, e.g., from about 100 pL/minute to about 200 pL/minute, e.g., about 120 pL/minute, e.g., less than 1000 pL/minute, e.g., less than 500 pL/minute, e.g., less than 300 pL/minute, e.g., less than 200 pL/minute).

In certain embodiments, the biofluid collection and sensing device comprises a flow rate sensor for measuring a flow rate of the biofluid through the at least one microfluidic or nanofluidic channel. In certain embodiments, the biofluid collection and sensing device comprises a temperature sensor for measuring a temperature of the body part (e.g., skin of a user) to which the device is in physical contact and/or a temperature of the biofluid and/or a temperature of a surrounding environment (e.g., and comprising a pressure sensor for measuring a pressure value exerted by the biofluid in the at least one microfluidic or nanofluidic channel). In certain embodiments, the biofluid collection and sensing device comprises a sweat rate sensor for measuring the rate at which the biofluid is received from and/or is emanated from a user of the device. In certain embodiments, the biofluid collection and sensing device comprises a conductivity sensor for measuring a conductivity of the received biofluid.

In certain embodiments, the biofluid collection and sensing device comprises an electronic circuit operably connected to the plurality of semiconductor sensors, wherein the electronic circuit operates the plurality of semiconductor sensors and/or produces and/or transmits signals representative of measured data from the plurality of semiconductor sensors corresponding to a presence and/or amount of the one or more biomarkers [e.g., wherein the electronic circuit comprises circuitry disposed on a printed circuit board (e.g., a flexible printed circuit board)] [e.g., wherein the electronic circuit comprises integrated circuit components disposed on the biofluid collection and sensing device (e.g., on a substrate of the biofluid collection and sensing device)] (e.g., and/or wherein the circuit operates a flow rate sensor, a temperature sensor, a pressure sensor, and/or a conductivity sensor, and/or produces and/or transmits signals representative of measured data from the flow rate sensor, the temperature sensor, the pressure sensor, and/or the pH sensor).

In certain embodiments, the circuit configured to detect in real-time (e.g., and continuously) the presence and/or concentration of at least one of (e.g., each of, e.g., one or more of, e.g., two or more of) the one or more biomarkers in the biofluid by the determination of a change in the electrical conductivity of at least one semiconductor sensor.

In certain embodiments, the circuit operates the plurality of semiconductor sensors and/or to produce and/or transmit signals representative of measured data from the plurality of semiconductor sensors, the electronic circuit comprising a plurality of FET devices.

In certain embodiments, the electronic circuit includes analog readout circuitry and/or analog-to-digital converters comprising metal-gate FET devices fabricated in the same circuit technology as the semiconductor sensors.

In certain embodiments, the circuit is configured to detect the presence and/or concentration of a plurality of different biomarkers in the biofluid by the determination of a differential signal, wherein the differential signal is derived from a control signal from a control sensor and a biomarker-specific signal from a functionalized sensor.

In certain embodiments, the biofluid collection and sensing device comprises an electronic circuit configured to manage and/or monitor energy consumption by the device.

In certain embodiments, the biofluid collection and sensing device comprises a wireless communication element (e.g., antenna) for transmitting data and/or signals measured and/or calculated by the biofluid collection and sensing device to an external device (e.g., processor of a web-based server, home computer, smart phone, mobile computing device, or the like).

In certain embodiments, at least one of the plurality of semiconductor sensors is a potassium sensor comprising an FD-FET sensor and either (i) an 18-crown ether or (ii) an ion selective membrane (e.g., wherein the ion selective membrane comprises polyvinyl chloride, bis(2-ethylehexyl) sebacate (DOS), sodium tetraphenylborate (NaTPB), and valinomycin (potassium ionophore)).

In certain embodiments, at least one of the plurality of semiconductor sensors is a sodium sensor comprising an FD-FET sensor and either (i) a 15-crown ether or (ii) an ion selective membrane (e.g., wherein the ion selective membrane comprises polyvinyl chloride, bis(2-ethylehexyl) sebacate (DOS), sodium tetrakis(3,5-bis(trifluoromethyl) phenyl) borate (Na-TFPB), and sodium ionophore X).

In certain embodiments, the biofluid collection and sensing device comprises a fixture module (e.g., one or more acrylate-based, biocompatible, and/or medical grade adhesives or tapes, e.g., one or more mechanically fastened straps) for disposing (e.g., affixing) the device on the body part (e.g., skin of a wearer) [e.g., wherein the fixture module includes a temporary (e.g., reversible) adhesive, is water-resistant, and has an external surface area of about 40 cm² or less] (e.g., wherein the fixture module has an external surface area of about 5 cm² or less).

In certain embodiments, the interface (e.g., a substrate) and/or interface surface has an external surface area (e.g., in contact with the human body) in a range from about 1 mm² to about 40 cm².

In certain embodiments, the biofluid collection and sensing device has a weight in a range from about 125 mg to about 1 g (e.g., wherein the device is designed to be carried by a human body in contact with an outer surface or skin of the human body).

In one aspect, the present disclosure is directed to a wearable apparatus comprising the biofluid collection and sensing device described herein [e.g., wherein the wearable apparatus is a member selected from the group consisting of a patch (e.g., an adhesive patch, e.g., a flexible adhesive patch), a wrist-band, a head-band, a bandage, a sock, a glove, an arm-band, a waist-band, an ankle-band, and a knee-band].

In certain embodiments, the wearable apparatus of claim 34 comprises a skin patch (e.g., a flexible skin patch).

In certain embodiments, the wearable apparatus comprises an electronic circuit that processes data and/or analyzes and/or transmits signals provided by the bio-fluid collection and sensing device (e.g., the sensor chip, e.g., wherein the sensor chip is a plug-in for the apparatus, e.g., a modular and/or disposable plug-in).

In certain embodiments, the wearable apparatus comprises a wireless communication element (e.g., antenna) for transmitting data and/or signals measured and/or calculated by the apparatus (e.g., a wearable object, e.g., a watch or band, into which the biofluid collection and sensing device is operably connected) to an external device (e.g., processor of a web-based server, home computer, smart phone, mobile computing device, or the like).

In one aspect, the present disclosure is directed to a method of using a biofluid (e.g., sweat, e.g., human sweat) collection and sensing device (e.g., wearable device). The method comprises affixing the biofluid collection and sensing device of any one of claims 1 to 32 to a human body, wherein the interface and/or the interface surface of the biofluid collection and sensing device is in contact with a surface (e.g., skin) of the human body.

In certain embodiments, the method includes tagging (e.g., scanning) the device with a mobile device (e.g., a mobile phone device) to trigger the device (i) to begin collection and sensing and/or (ii) to initiate signal transmission (e.g., wireless electronic signal transmission) from the biofluid collection and sensing device to the mobile device.

In one aspect, the present disclosure is directed to a method of sensing (e.g., the presence and/or quantity of) one or more biomarkers in a biofluid using a biofluid (e.g., sweat, e.g., human sweat) collection and sensing device (e.g., wearable device). The method comprises receiving (e.g., continuously), by a processor of a computing device (e.g., an analysis module of a biofluid collection and sensing device, e.g., a mobile device), data from a biofluid collection and sensing device, wherein the data comprises two or more signals comprising a control signal and a biomarker signal. The control signal corresponds to an electronic signal from a control semiconductor sensor in contact with a biofluid (e.g., wherein the control semiconductor sensor has an unmodified gold gate). The biomarker signal corresponds to an electronic signal from a functionalized semiconductor sensor in contact with said biofluid (e.g., wherein the functionalized semiconductor sensor comprises selective moieties). The method comprises calculating (e.g., continuously), by the processor, a differential biomarker signal using the control signal and the biomarker signal (e.g., wherein the differential signal is a difference or a ratio of the control signal and the biomarker signal).

BRIEF DESCRIPTION OF THE DRAWINGS

The foregoing and other objects, aspects, features, and advantages of the present disclosure will become more apparent and better understood by referring to the following description taken in conjunction with the accompanying drawings, in which:

FIG. 7A is a reaction diagram for the functionalization of gold gates with crown ethers, according to an illustrative embodiment;

FIG. 7B is a diagram depicting the surface of a gold gate functionalized with an 18-crown ether used for potassium ($K^+$) sensing, according to an illustrative embodiment. The gold gate may be electrically connected and biased notably to perform electrodeposition of polymer on the gate;

FIG. 7C is a diagram depicting the surface of a gold gate functionalized with a 15-crown ether for sodium ($Na^+$) sensing, according to an illustrative embodiment. The gold gate may be electrically connected and biased notably to perform electrodeposition of polymer on the gate;

Figure 1:
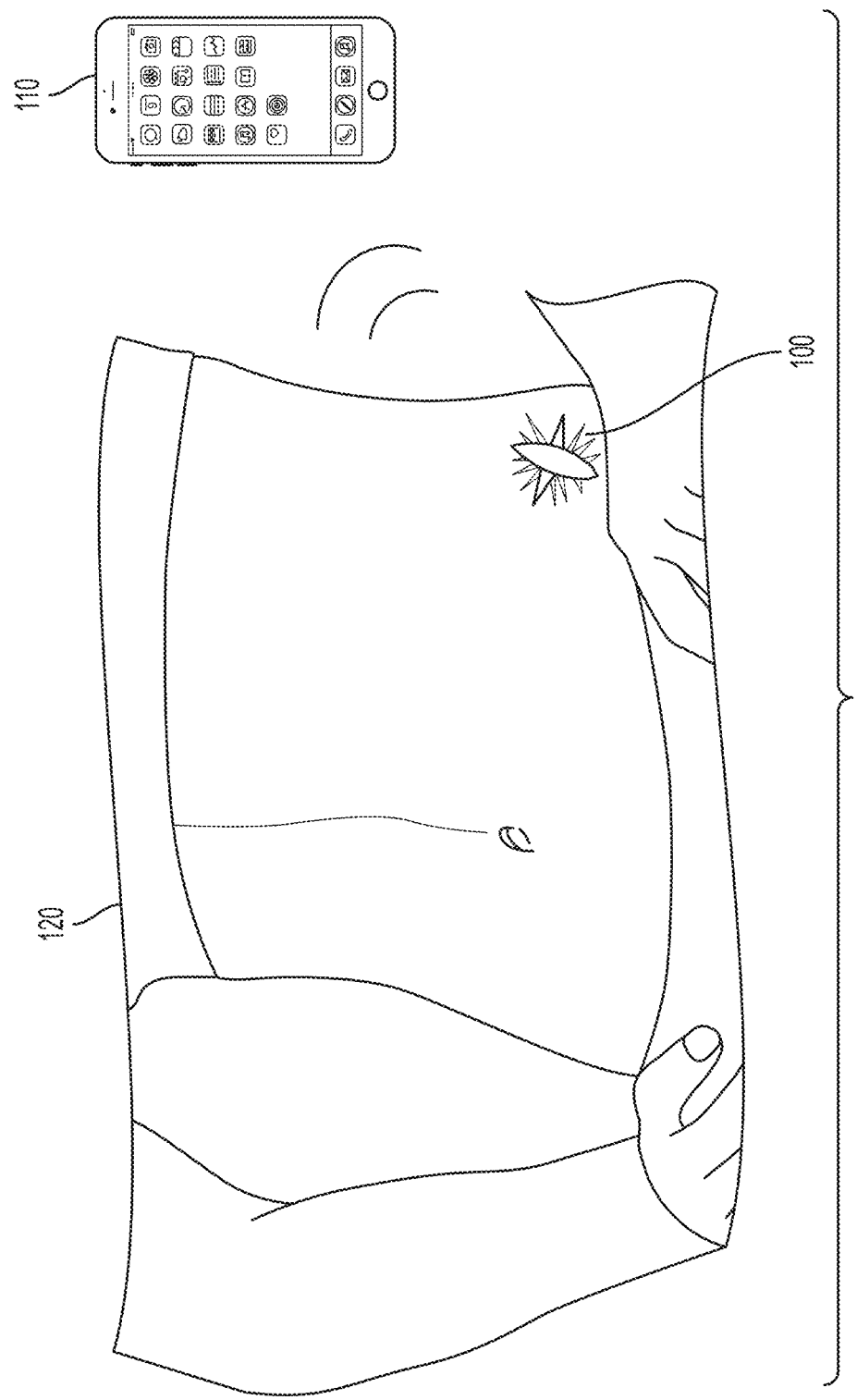
FIG. 1 shows a depiction of a wearable biofluid collection and sensing device affixed to the skin of a user, where the device includes a remote communication module for transmitting data from the wearable device to a mobile device, according to an illustrative embodiment.

The features and advantages of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements.

DETAILED DESCRIPTION

It is contemplated that systems, architectures, devices, methods, and processes of the claimed invention encompass variations and adaptations developed using information from the embodiments described herein. Adaptation and/or modification of the systems, architectures, devices, methods, and processes described herein may be performed, as contemplated by this description.

Throughout the description, where articles, devices, systems, and architectures are described as having, including, or comprising specific components, or where processes and methods are described as having, including, or comprising specific steps, it is contemplated that, additionally, there are articles, devices, systems, and architectures of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

Documents are incorporated herein by reference as noted. Where there is any discrepancy in the meaning of a particular term, the meaning provided in this document is controlling.

Headers are provided for the convenience of the reader— the presence and/or placement of a header is not intended to limit the scope of the subject matter described herein.

As used herein, unless otherwise clear from context, (i) the term "a" may be understood to mean "at least one"; (ii) the term "or" may be understood to mean "and/or"; (iii) the terms "comprising" and "including" may be understood to encompass itemized components or steps whether presented by themselves or together with one or more additional components or steps; and (iv) where ranges are provided, endpoints are included.

As used herein, the terms "about" or "approximately", when used herein in reference to a value, refers to a value that is similar, in context to a referenced value. In general, those skilled in the art, familiar with the context, will appreciate the relevant degree of variance encompassed by "about" or "approximately" in that context. For example, in some embodiments, the terms "about" or "approximately" may encompass a range of values that within 25%, 20%, 19%, 18%, 17%, 16%, 15%, 14%, 13%, 12%, 11%, 10%, 9%, 8%, 7%, 6%, 5%, 4%, 3%, 2%, 1%, or less of the referred value.

As used herein, the term "continuous," as in a continuous biomarker measurement, refers to performing a series of measurements (e.g., of the presence and/or quantity of a biomarker) without a substantial time interval between each measurement. For example, continuous measurements may be performed at a rate of one measurement every ten minutes, one measurement every five minutes, one measurement per minute, one measurement every 30 seconds, one measurement every 5 seconds, or faster rates.

In certain embodiments, a continuous measurement can occur in substantially "real-time" such that the concentration value of an analyte measured by the device is the concentration present in sweat without a substantial delay or latency on the timescale of physiological processes (e.g., on a scale of five minute or greater). For example, the device may display a "snapshot" of the concentration of an analyte in the biofluid (e.g., every 5 minutes, 1 minute, 30 seconds or less). In certain embodiments, the continuous measurements are performed at a higher frequency (e.g., every second or every several milliseconds) providing a continuous analyte data stream faster than the physiological timescale.

As used herein, the term "substantially" refers to the qualitative condition of exhibiting total or near-total extent or degree of a characteristic or property. For example, a substantially constant value may vary in time by 20%, 15%, 10%, 9%, 8%, 7%, 6%, 5%, 4%, 3%, 2%, 1%, or less of the constant value.

Details regarding various embodiments of a biofluid (e.g., sweat, e.g., human sweat) collection and sensing device are described herein. The biofluid collection and sensing device may include an on-chip integration of arrays of functionalized semiconductor sensors [e.g., field-effect transistors (FETs), e.g., ion-sensitive FETs (ISFETs), e.g., fully depleted FETs (FD-FETs)], fluidics (e.g., microfluidic channels, e.g., nanofluidic channels), and/or a reference electrode (e.g., a quasi-reference electrode). The gates of the semiconductor sensors can be functionalized with a plurality of selective moieties (e.g., molecules, aptamers, antibodies, and/or enzymes) or polymer membranes for the selective detection and/or quantification of different target analytes including, for example, ions, molecules, proteins, enzymes, hormones, and bacteria. The use of multiple sensors enables multi-parametric sensing (e.g., the detection of multiple analytes simultaneously).

In certain embodiments, the devices described herein collect and/or channel sweat from a user of the device for the detection and/or quantification of one or more biomarkers in the sweat. Biomarkers can be monitored, for example, for purposes of health, wellness, and/or sports. In certain embodiments, a biofluid collection and sensing device provides information about the health, wellness, and/or other physical, mental, or emotional condition of the wearer in substantially real time (e.g., continuously).

The one or more biomarkers may include one or ions (e.g., chloride, sodium, potassium, calcium, ammonium, silver ions, and chromium ions), hormones and/or steroids (e.g., steroid hormones, dehydroepiandrosterone (DHEA), estrogen, vasopressin, cholesterol, adrenalin, cortisol, and cortisone), proteins (e.g., cytokines, CFP, ESAT-10 (a tuberculosis biomarker), and neuropeptides), metabolites (e.g., alcohol, lactic acid, lactate, urea, and creatinine), organic compounds: [e.g., vitamins (e.g., ascorbic acid), glucose, penicillin, and hydrogen peroxide], and/or other components. A listing of illustrative biomarkers that can be found in sweat and used in health monitoring applications is presented in Table 1.

TABLE 1

Biomarkers and their applications when measured using the devices described herein.

| Biomarker | Health Monitoring Applications |
|---|---|
| Chloride | Monitoring cystic Fibrosis |
| Potassium | Monitoring muscle activity |
| | Monitoring kalemia related conditions |
| Ethanol | Monitoring alcohol intoxication |
| Cortisol | Monitoring stress levels |
| Urea | Monitoring renal functions |
| | Detecting kidney failure |
| Lactate | Monitoring exertion level (e.g., during anaerobic activity) |
| Cytokines | Monitoring immune system health |
| | Monitoring infection |
| Neuropeptide | Monitoring level of alertness |
| | Monitoring levels if anti-depressive or anti-stress neuropeptides |
| Ammonium | Monitoring patients in critical care (may be sensitive to movement) |
| Chromium | Monitoring type II diabetes |
| | Monitoring insulin resistance |
| Glucose | Monitoring diabetes |

FIG. 1 shows an illustrative example of a wearable biofluid collection and sensing device 100. Wearable device 100 is affixed to the skin of user 120, for example, with a biomedical adhesive. Wearable device 100 comprises an interface for efficiently collecting sweat from the skin of user 120. The surface area of the interface in contact with a body of the wearer may be from about 1 mm$^2$ to about 40 cm$^2$. This interface may include sealing elements, membranes or localized surface treatments or patterning to, for example, provide hydrophobicity, to selectively prevent contamination of the collected biofluid collected from external sources (e.g., from rain, e.g., from old, mixed, and/or degraded biofluid flowing from other areas of the subject body).

Wearable device 100 includes microfluidic and/or nanofluidic channels, one or more fluid inlets, one or more fluid outlets, and a micro-pump. These features work in synergy to provide for controlled collection of sweat from the skin of user 120. For example, each micro pump can be patterned with defined geometries (e.g., arborescent structures, e.g., pillar arrays) to facilitate the controlled capillary action-based flow of sweat once it is collected via the inlet(s) of device 100. The collected sweat flows towards over a plurality of semiconductor sensor arrays used to detect and/or quantify biomarkers in the sweat.

The plurality of semiconductor sensors include one or more arrays of field effect transistors (FETs) (e.g., ion sensitive FETS (ISFETs), e.g., fully depleted FETs (FD-FETs)). For example, one or more of the FETs may be a Fin-FET as described in U.S. Pat. No. 9,570,288, the entirety of which is incorporated herein by reference. The array(s) of FETs may include FETs with a ribbon architecture fabricated on a fully depleted silicon-on-insulator substrate with a buried oxide layer (an FD-SOI substrate). The present disclosure encompasses the recognition that the dimensions and design of the FD-SOI substrate allows for devices with less complex fabrication processes, improved electrostatic control of the FET, a decreased parasitic capacitance between source and drain, decreased leakage currents, and decreased power consumption compared to previous technology.

The FD-SOI substrate allows FD-FETs to be fabricated with a ribbon-like structure with less strict dimensional constraints. Thus, FD-FET sensors can be fabricated with a larger sensing surface area (e.g., for improved sensor signal) than was possible using previous approaches, while maintaining the excellent electrical properties of the FD-FET. For example, the surface area of the gate of the semiconductor sensor (e.g., an FD-FET sensor) can be in a range from about 1 $\mu m^2$ to about 1000 $\mu m^2$ or larger. In certain embodiments, the surface area of the gate of the semiconductor sensor (e.g., an FD-FET sensor) is in a range from about 35 $\mu m^2$ to about 150 $\mu m^2$.

In certain embodiments, the semiconductor sensors have liquid gates that are functionalized for the detection of selected biomarkers. For example, one or more of the sensors may have a gate that includes hafnium dioxide ($HfO_2$) (e.g., for use as a pH sensor). Each semiconductor sensor (e.g., the gate of each FET) is functionalized to detect and/or quantify a biomarker of interest (e.g., one of those biomarkers shown in Table 1). Wearable device 100 can also include sensors for measuring other properties of user 120 or the environment. For example, device 100 may include a temperature sensor (e.g. a diode-based temperature sensor), a flow rate sensor (e.g., an acoustic or optical flow meter, e.g., a calorimetric or thermal flow meter based on measurements of heat convection by a flowing fluid, e.g., a flow meter based on differential pressure measurement(s)), a conductivity sensor (e.g. a plurality of platinum electrodes or Ag/AgCl electrodes), an ionic strength sensor, a pressure sensor (e.g. a gauge-based pressure sensor, e.g., a Microelectromechanical system (MEMS)-based pressure sensor, e.g., a piezoresistive pressure sensor), and/or a pH sensor.

Data from these sensors can be used, for example to measure the rate at which user 120 is sweating and/or the total quantity of dissolved ions in the collected sweat. For example, rate of sweating can be an important factor in evaluating the health of user 120. In certain embodiments these measurements can be used to calibrate device 100. For example, an analyte signal from a given semiconductor sensor may be adjusted based on a temperature measurement to account for known changes in sensor sensitivity and/or specificity that accompany changes temperature. For example, an analyte signal from a given semiconductor sensor may be adjusted based on a flow rate measurement to account for known changes in analyte flux rate as a function of flow rate.

In order to facilitate non-invasive biomarker sensing, in certain embodiments, biofluid collection and sensing device 100 comprises a fixture module (e.g., a patch, e.g., an adhesive, e.g., a strap) which allows the device to be affixed directly to the skin of a user 120. The fixture module may have various properties related to adhesivity, hydrophilicity, hydrophobicity, permeability and impermeability to sweat solutes or solvent, electrical conductivity and insulation, and thermal conductivity and insulation. For example, the fixture module may be or include acrylate-based, biocompatible or medical grade adhesives or tapes or mechanically fastened straps (e.g., a Velcro® strap). In certain embodiments, the fixture module and/or the wearable device includes perforations such that it is more permeable to water vapor. This can make the device more comfortable to wear.

Wearable device 100 includes an electronic circuit interconnected to the plurality of semiconductor sensors. The circuit is designed to operate the plurality of semiconductor sensors. For example, the circuit can produce and/or transmit signals representative of measured data from the plurality of semiconductor sensors. In certain embodiments, the circuit can process the measured data and store the processed and/or unprocessed data in memory (e.g., in an internal flash memory, e.g., in an external memory). In certain embodiments, the electronic circuit includes circuitry disposed on a printed circuit board (e.g., a flexible printed circuit board). In other embodiments, the electronic circuit includes integrated circuit components disposed on the biofluid collection and sensing device (e.g., on a wafer of the biofluid collection and sensing device).

The circuit is configured to continuously detect the presence and/or concentration of at least one biomarker in the biofluid. For example, the presence and/or concentration of a biomarker may be determined by measuring a change in the electrical conductivity of at least one of the semiconductor sensors. In certain embodiments, the electronic circuit includes analog readout circuitry and/or analog-to-digital converters comprising metal-gate FET devices, for example, fabricated using the same or a similar approach to that used to fabricate the semiconductor sensors. In certain embodiments, the electronic circuit also monitors and/or manages the energy usage (e.g., energy consumption) of the device.

The electronic circuit can also produce and/or transmit signals representative of measured data from the wearable device 100 for storage and/or display on mobile device 110. For example, wearable device 100 can include a wireless communication element (e.g., antenna) for transmitting data and/or signals measured and/or calculated by device 100 to an external device (e.g., mobile device 110, the processor of a web-based server, or a personal computer). For example, user 120 may tag (e.g., scan) wearable device with a camera or with a wireless communication module (e.g. a Near Field Communications (NFC) module, e.g., a Wi-Fi module, e.g., a Bluetooth® module) of mobile device 110 to obtain communication parameters from the wearable device 110. The communication parameters can include information (e.g., a wireless network address) for interfacing with the wearable device 110 via a wireless network. The data can be transmitted via wireless Ethernet, Bluetooth®, or radio and received by a receiver of mobile device 110. Mobile device 110 may include, for example, an application for, upon receipt of biomarker analysis data transmitted from wearable device 100, compiling, analyzing, storing, and/or presenting the transmitted data. For example, a plot of measured biomarker levels over time or average biomarker levels over a given time interval may be presented on the display of mobile device 110. In certain embodiments, an audible alarm and/or buzzer may be sounded (e.g., from mobile device 110 or from device 100) if a measured biomarker level is above or below a predefined threshold.

In certain embodiments, wearable device 100 is disposable (e.g., after a certain period of wear the device is discarded and replaced). In certain embodiments, the device is designed for approximately 24 hours of wear, after which it may be disposed. In other embodiments, the device is designed to be replaced on a weekly or monthly basis.

Figure 2:
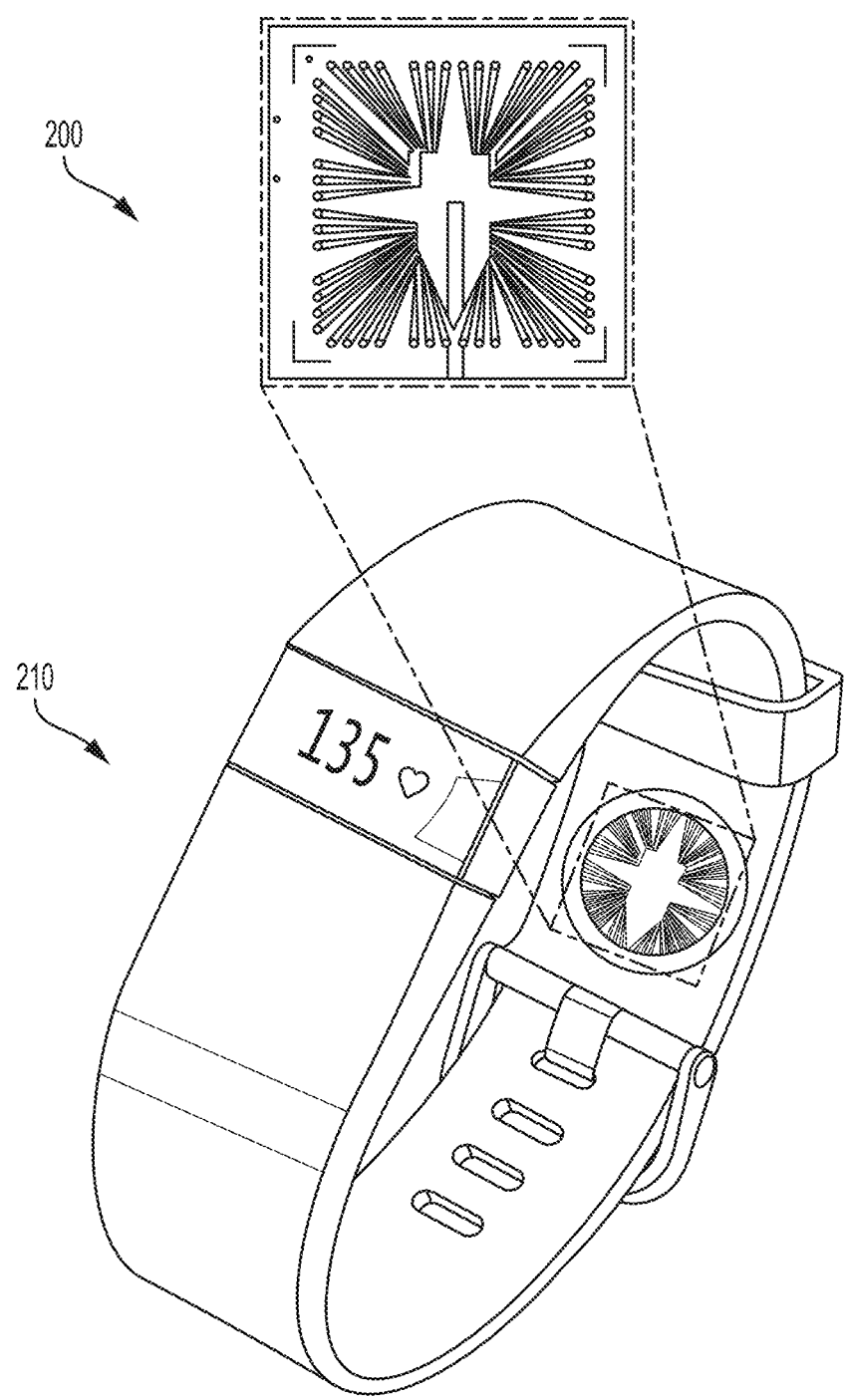
FIG. 2 shows a depiction of an exemplary biofluid collection and sensing device housed in the wrist band of a wearable device.

The biofluid collection and sensing device can also be housed on or in a wearable article or device. For example, the wearable article or device may be a patch (e.g., an adhesive patch, e.g., a flexible adhesive patch affixed to the skin as shown in FIG. 1), a wrist-band, a head-band, a bandage, a sock, a glove, an arm-band, a waist-band, an ankle-band, or a knee-band. For example, the biofluid collection and sensing device may comprise a plugin module that is compatible with a given smart watch. FIG. 2 shows an exemplary biofluid collection and sensing device 200 device housed in the wrist band of wearable device 210. A variety of wearable devices are commercially available that can measure the physical characteristics of a wearer such as heart rate and number of steps taken per interval of time. Certain embodiments of the biofluid collection and sensing devices described herein provide complementary health information for assessing the health and wellness of a wearer. In certain embodiments, biofluid collection and sensing device 200 is functionally connected to wearable device 210 such that the two devices can share power and other resources (e.g., for data presentation, data storage, and wireless communication). For example, biofluid collection and sensing device 200 can access other functionalities of wearable device 210, to transmit information via Bluetooth® and perform other common functions.

Figure 3:
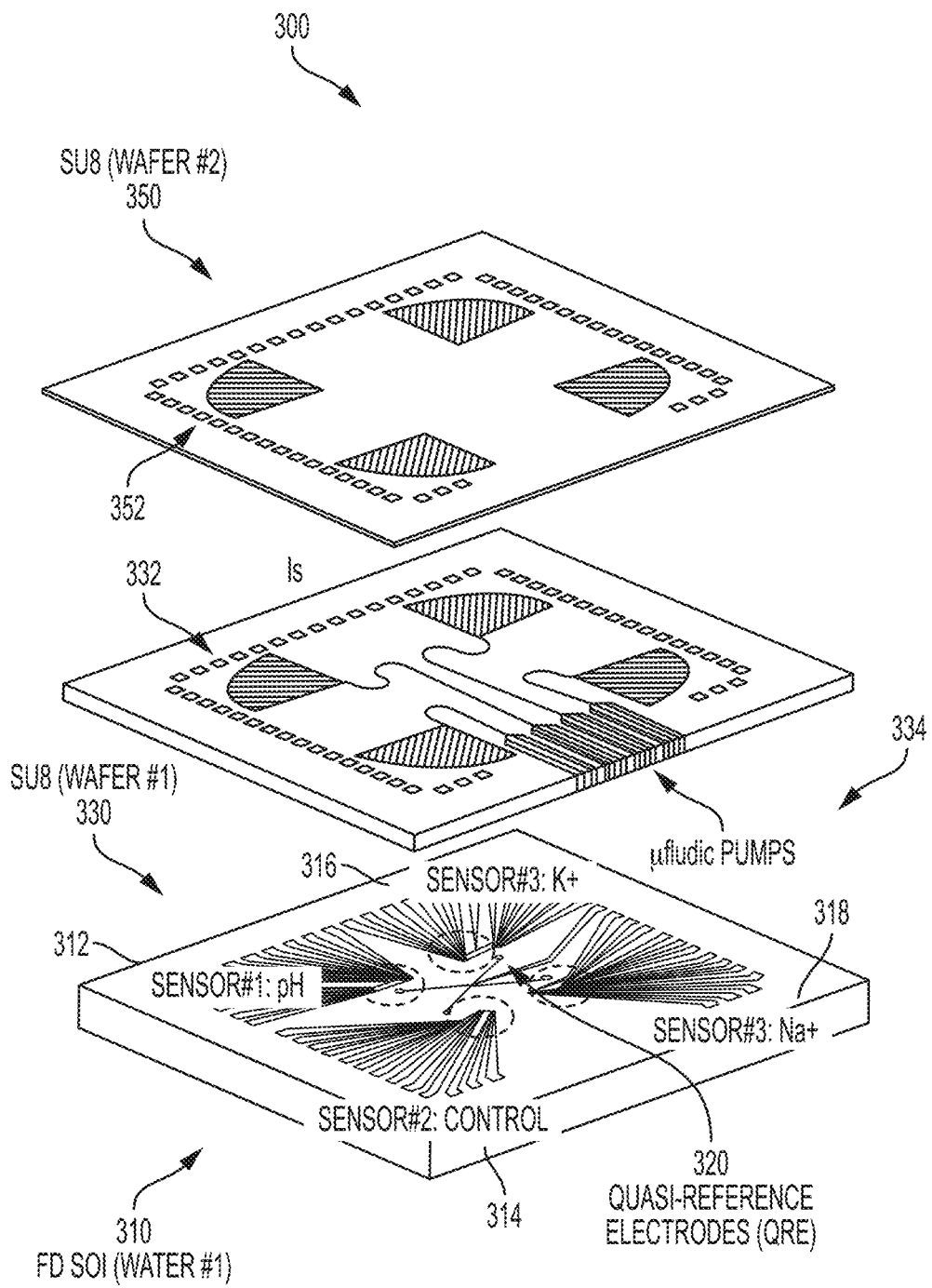
FIG. 3 is a schematic diagram depicting the design of a biofluid collection and sensing device that includes multiple microfluidic layers for biofluid collection and channeling, according to an illustrative embodiment.

FIG. 3 is a schematic diagram of the layered structure of a biofluid collection and sensing device 300, according to an illustrative embodiment. Biofluid collection and sensing device 300 includes a first sensing layer 310. Sensing layer 310 includes a substrate such as a bulk silicon wafer, a partially-depleted SOI (PD-SOI) substrate, or a fully depleted silicon on insulator (FD SOI) substrate (e.g., an ultra-thin body and buried oxide FD-SOI (UTBB-FD-SOI)). An FD-SOI substrate includes a base silicon wafer, a thin buried oxide layer over the silicon wafer, and a thin layer of silicon on top of the oxide. The buried oxide (BOx) layer, for example, can have a thickness in a range from about 5 nm to about 50 nm. In certain embodiments, the buried oxide layer is about 20 nm thick. The thin top layer of silicon, for example, can have a thickness in a range from about 5 nm to about 40 nm. In certain embodiments, the top layer of silicon is about 25 nm thick. The surface of sensing layer 310 includes four semiconductor sensor arrays including a pH sensor 312, a control sensor 314, a potassium ($K^+$) sensor 316, and a sodium ($Na^+$) sensor 318. FIG. 4B is an illustration 450 from a top-down view of an illustrative embodiment of sensing layer 310.

The surface of each of sensors 312, 314, 316, and 318 can be prepared and/or functionalized for the detection and/or quantification of a biomarker of interest. For example, pH sensor 312 has a gate that includes $HfO_2$, which is pH sensitive. FIG. 7A shows a general reaction diagram 700 for the functionalization of the gold gate of a semiconductor sensor (e.g., an ISFET, e.g., an FD ISFET) with a crown ether

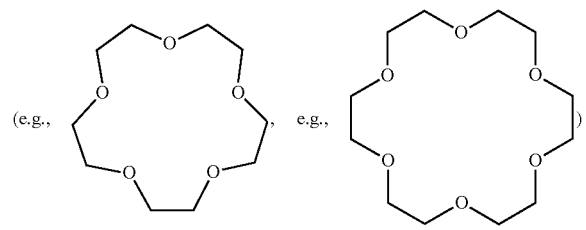 [SMILES: C1COCCOCCOCCOCCO1 ; C1COCCOCCOCCOCCOCCO1]

in order to prepare an ISFET (sensors 316 and 318). The functionalization of the gold gate is based on the gold-thiol interactions between thiolated ion-sensitive crown ethers and the gold gate of the sensor. The hydroxyl group of the crown ether is converted to a sulfonate (leaving group), for example, using toluenesulfonyl chloride. A nucleophilic substitution is then performed (e.g., using 2,2'-ethylenedi-oxy-diethanedithiol to obtain a thiol-functionalized crown ether. The thiol-functionalized crown ether is then bound to the surface of the gold gate of each semiconductor sensor via gold-thiol binding.

Each crown ether has a high affinity for a particular ion, depending largely on the "size" of (e.g., number of atoms in) the crown. For example, an 18-crown ether has a high affinity for $K^+$ Potassium ($K^+$) sensor 316 can be prepared by functionalizing the surface with 18-crown ethers, as shown in illustration 710 of FIG. 7B. The concentration of the crown ether on the sensor surface is controlled via the concentration of the crown ether added to a functionalization solution with which the sensor is contacted and the amount of time this contact occurs. The conductivity of sensor 316 will change (e.g., a voltage measured at a constant current will change) based on the concentration of $K^+$ in the biofluid. In a similar manner, sodium ($Na^+$) sensor 318 can be prepared according to the functionalization chemistry shown in illustration 720 of FIG. 7C. A 15-crown ether has a high affinity for $Na^+$.

Alternatively, a gold gate or a gate comprising another noble metal gate—with an external connection pad that can be electrical biased—can be modified chemically or electrochemically, to provide the desired functionality. This functionality may include polymers, conducting polymers, polymer membranes, and or molecules which can be chemically or electrochemically deposited or undergo electrochemical functionalization once immobilized.

In certain embodiments an ion to electron converter such as PEDOT:PSS is used in conjunction with ion selective membranes to provide sensing selectivity. For a sodium sensor, the ion selective membrane can be a solution composed of polyvinyl chloride (e.g., with a high molecular weight), bis(2-ethylhexyl) sebacate (DOS), sodium tetrakis [3,5-bis(trifluoromethyl)phenyl] borate (Na-TFPB), and sodium ionophore X in tetrahydrofurane that is drop-casted on the top of the sensor. For a potassium sensor, the ion selective membrane can be a solution composed of polyvinyl chloride (e.g., with a high molecular weight), bis(2-ethylhexyl) sebacate (DOS), sodium tetraphenylborate (NaTPB), and valinomycin (potassium ionophore) in cyclohexanone that is drop-casted on the top of the sensor.

Returning to FIG. 3, sensing layer 310 optionally includes a QRE 320, which is positioned near each sensor array. QRE 320 may be a silver/silver chloride (Ag/AgCl) QRE. The Ag/AgCl QRE can be prepared by chlorinating silver. For example, a silver electrode with the pattern of QRE 320 may be deposited (e.g., using electrodeposition) and patterned using standard semiconductor fabrication methods. The silver surface can then be chlorinated chemically [e.g., in the presence of an oxidizing material and chloride ions ($Cl^-$), e.g., iron (III) chloride ($FeCl_3$)] or electrochemically (e.g., by applying an anodic current or by cyclic voltammetry to the electrode in the presence of $Cl^-$).

Figure 6A:
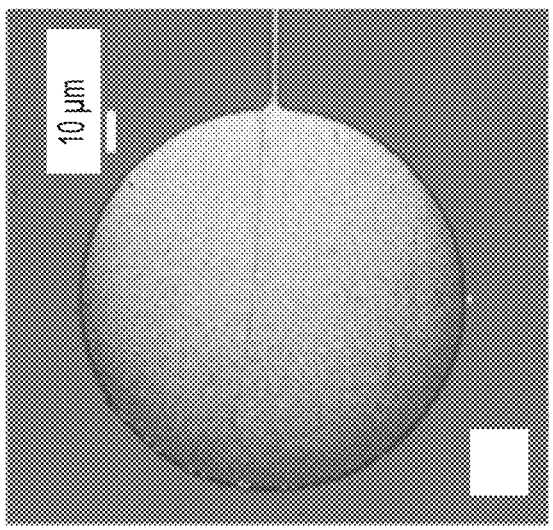
FIG. 6A is an optical micrograph of a silver/silver chloride (Ag/AgCl) QRE before chlorination (e.g., a silver electrode), according to an illustrative embodiment.
Figure 6B:
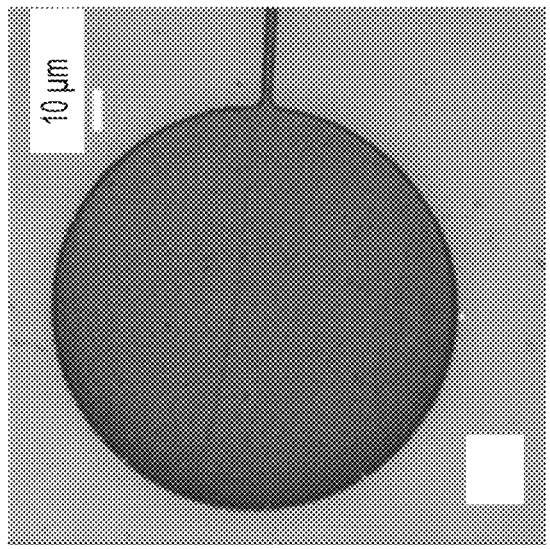
FIG. 6B is an optical micrograph of a fabricated Ag/AgCl QRE after chlorination, according to an illustrative embodiment.
Figure 6C:
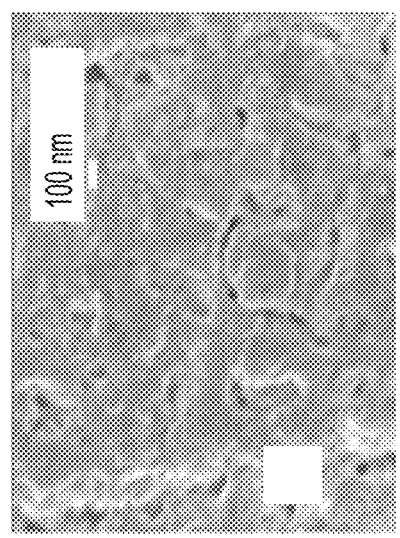
FIG. 6C is an SEM micrograph of a fabricated Ag/AgCl QRE before chlorination (e.g., a silver electrode), according to an illustrative embodiment.
Figure 6D:
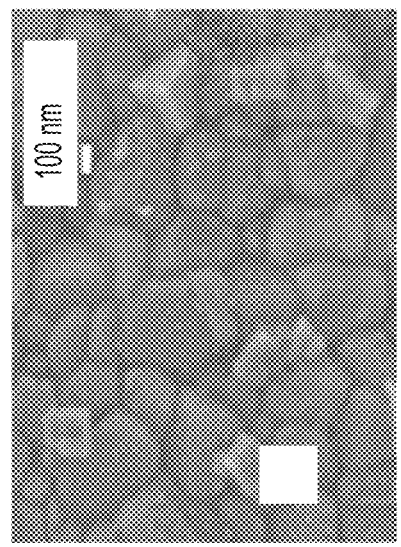
FIG. 6D is an SEM micrograph of a fabricated Ag/AgCl QRE after chlorination, according to an illustrative embodiment.

An illustrative example of a silver surface before chlorination is shown in FIG. 6A (optical micrograph) and FIG. 6C (SEM micrograph), and an illustrative example of a Ag/AgCl QRE surface after chlorination is shown in FIG. 6B (optical micrograph) and FIG. 6D (SEM micrograph). A protective membrane may be deposited onto the QRE. The deposited volume of the membrane should be sufficient to cover and shield the reference electrode from interfering ions such as $Cl^-$ for Ag/AgCl and also to slow down its dissolution. Such protective membranes may include polyvinyl butyral (PVB) loaded with NaCl or a chloride containing salt, Nafion® or self-assembled monolayers.

Returning to FIG. 3, in certain embodiments, sensing layer 310 has two layers such that the semiconductor sensors (sensors 312, 314, 316, and 318) and QRE 320 are on different layers (e.g., planes) of the device. For example, the semiconductor sensors (e.g., (sensors 312, 314, 316, and 318) may extend in a first plane while the reference electrode (e.g., QRE 320) extends in a second plane. The plane comprising the QRE can be above or below the plane comprising the semiconductor sensor. In certain embodiments, the biofluid collection and sensing device does not have a QRE or any other reference electrode.

The biofluid collection and sensing device also includes one or more microfluidic layers. The biofluid collection and sensing device shown in FIG. 3 includes a microfluidic layer 330, which is above sensing layer 310, and microfluidic layer 350 above microfluidic layer 330. Microfluidic layer 330 includes a plurality of microfluidic and/or nanofluidic channels 332 and at least one micro pump 334. Microfluidic layer 350 acts as an interface between the biofluid collection and sensing device and a wearer of the device. The two integrated microfluidic layers 330 and 350 allow a biofluid (e.g., sweat) to be collected from a user of the device via one or more inlets 352 and conducted to the semiconductor sensors. The size, density (e.g., number per unit of area), and arrangement of inlets 352 is designed such that a biofluid may be efficiently collected and channeled into the device. Inlets 352 can have an arborescent structure, as shown in FIG. 3. The dimensions of each branch of the arborescent structure has a width of about tens of micrometers and a length of a few hundred (e.g., one hundred, two hundred, three hundred, four hundred, or five hundred) micrometers.

Fluid flow through the microfluidic and/or nanofluidic channels of the biofluid collection and sensing device is established by micro pump(s) 334, which act in synergy with entire microfluidic structure including the inlets 352, and microfluidic and/or nanofluidic channels to collect biofluid and maintain a constant flow rate. For example, the geometry of inlets 352 and the surface properties of the interface between the device and the skin of a user and microfluidic and/or nanofluidic channels facilitate the initial filling of the device with a biofluid via capillary action. Once the biofluid reaches micro pump(s) 352, flow is then controlled by, for example, a plurality of micropillars through capillary forces. European patent application No. 16188227.9 filed Sep. 10, 2016 and U.S. patent application Ser. No. 15/453,920 are both incorporated herein by reference in their entirety.

Figure 5A:
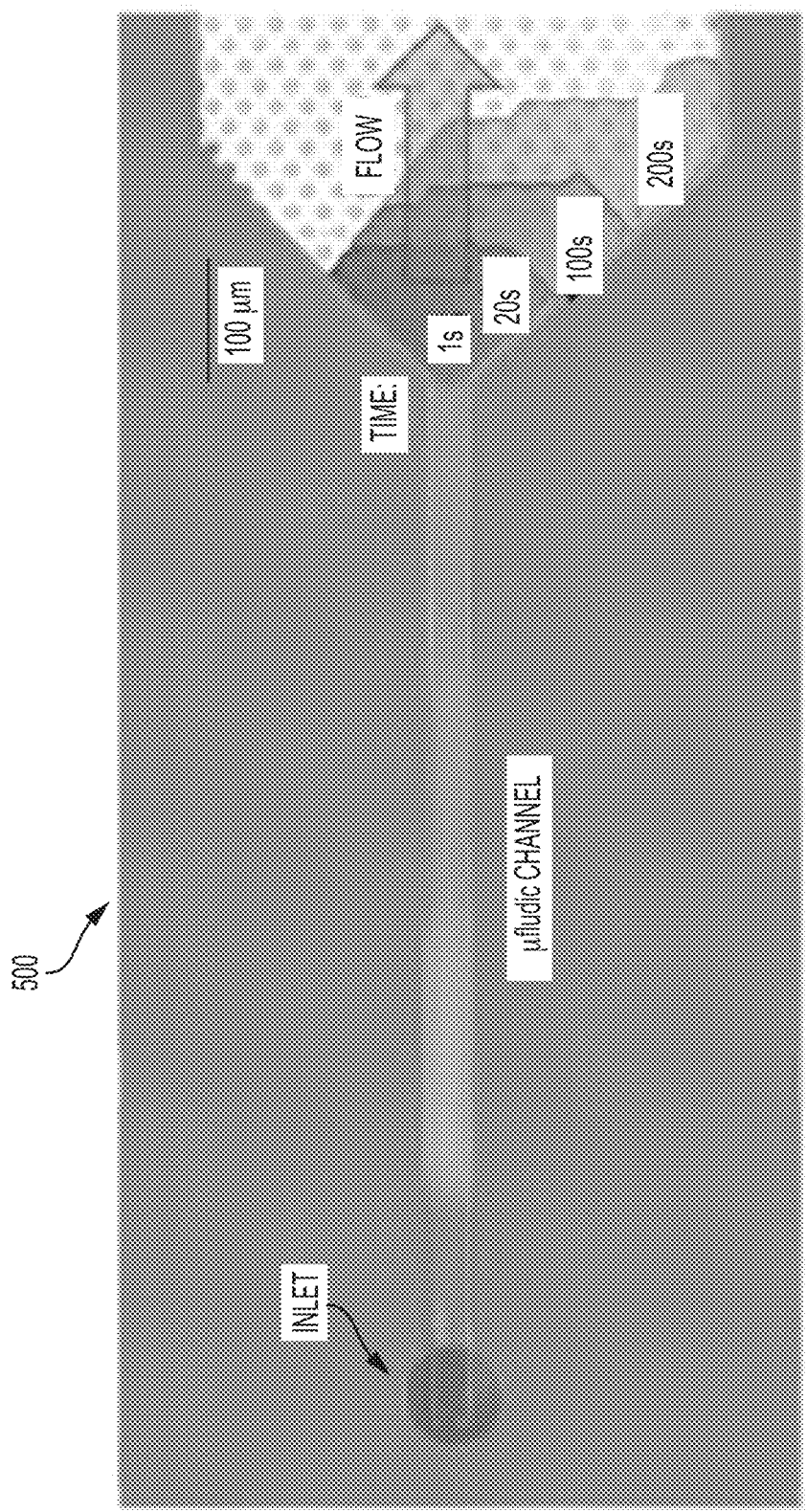
FIG. 5A is an optical micrograph of a microfluidic channel of a biofluid collection and sensing device with a time-lapsed image of the propagation of a biofluid into the microchannel of the device at various time points using a zero-energy micro pump, according to an illustrative embodiment.
Figure 5B:
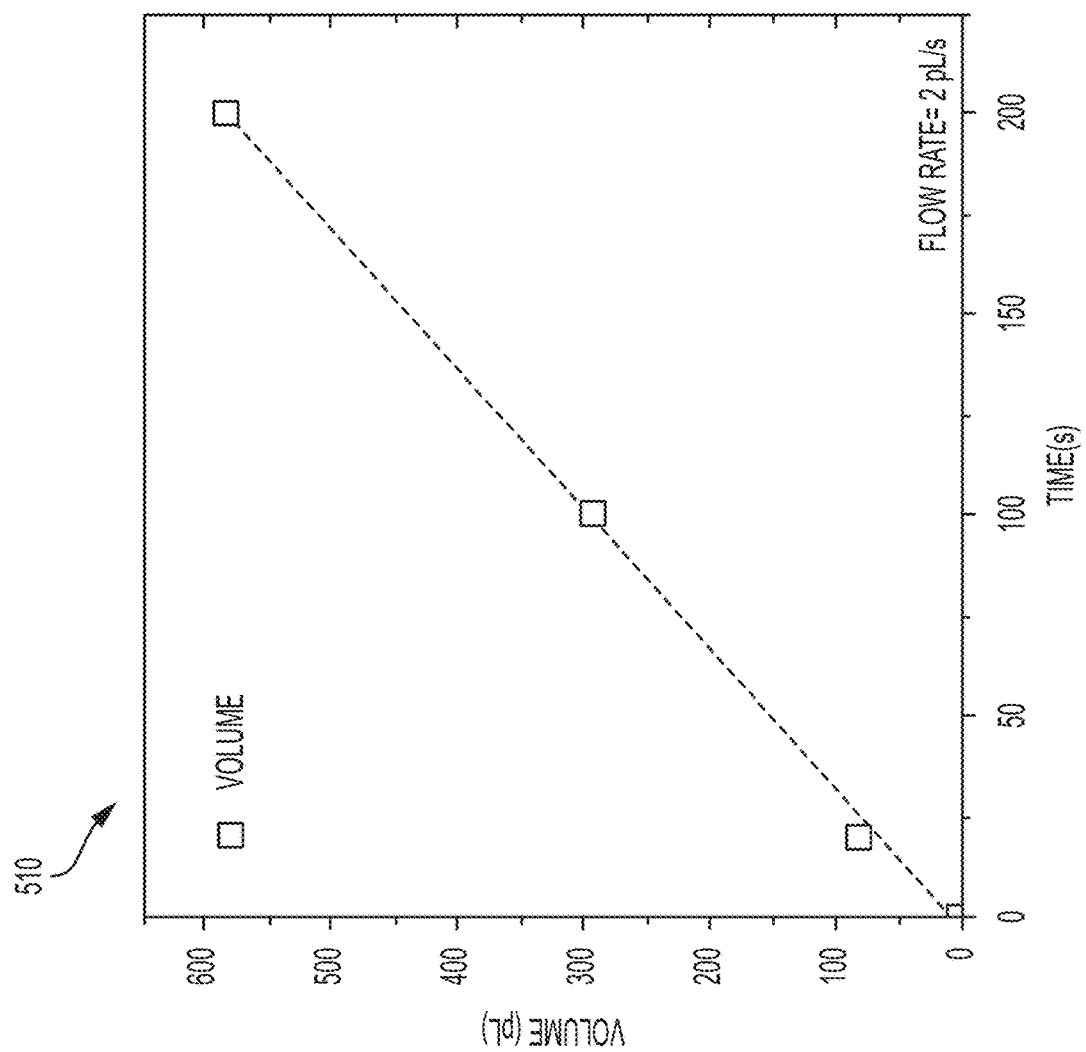
FIG. 5B is a plot of the volume of fluid inside the device shown in FIG. 5A versus time where the fluid flow is provided by a zero-energy micro pump, according to an illustrative embodiment.
Figure 5C:
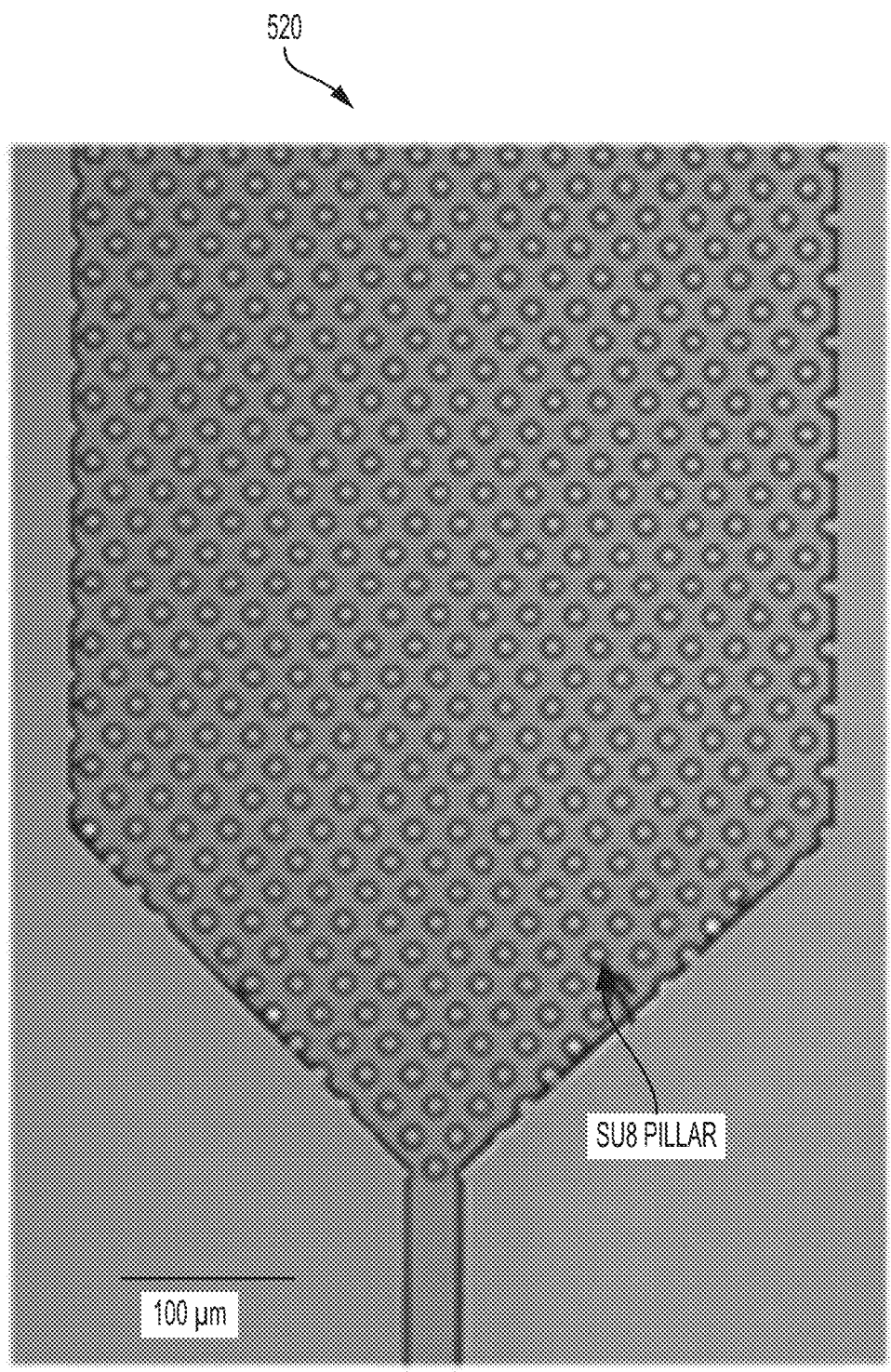
FIG. 5C is an optical micrograph of SU-8 micropillars of a zero-energy micro pump, according to an illustrative embodiment.

FIG. 5C is an optical micrograph 520 of SU-8 micropillars of an illustrative example of a micro pump of a bio-fluid collection and sensing device. The micro pump (e.g., via the arrangement, shape, and/or size of the micropillars) provides a substantially constant flow rate of biofluid into the device. For example, the flow rate can be in range from about 1 picoliters (pL)/minute to about 5 nanoliters (nL)/minute, from about 10 pL/minute to about 3 nL/minute, from about 50 pL/minute to about 1000 pL/minute, from about 100 pL/minute to about 200 pL/minute. In certain embodiments, the flow rate is less than or equal to about 1000 pL/minute, less than or equal to about 500 pL/minute, less than or equal to about 300 pL/minute, or less than or equal to about 200 pL/minute.

FIG. 5A is an optical micrograph 500 of a microfluidic channel of a biofluid collection and sensing device, according to an illustrative embodiment. The microchannel image in FIG. 5A includes a time-lapsed images of a biofluid propagating into the channel. Fluid propagation (e.g., flow) was provided by a zero-energy capillary pumping. FIG. 5B is a plot 510 of the volume of fluid in the device shown in FIG. 5A versus time. The slope of line shown in plot 510 shows that the flow rate of fluid through the example device was two picoliters/second (pL/s) (i.e., 120 pL/min).

In certain embodiments, the two or more microfluidic layers (e.g., microfluidic layers 330 and 350) are biocompatible. For example, the microfluidic layers can comprise a biocompatible material such as glass, silicon, aluminum oxide, silicon dioxide, other oxides, SU-8

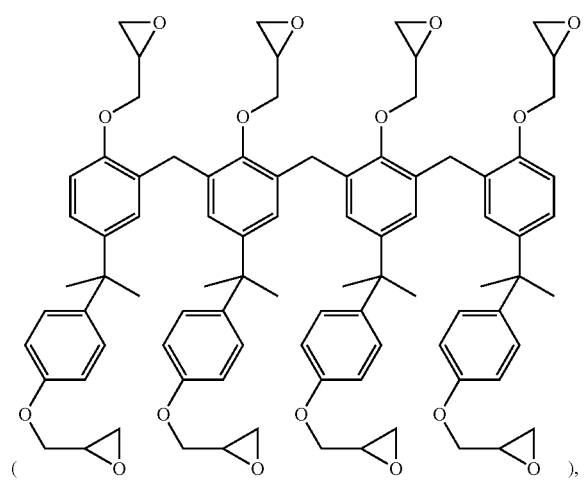

polydimethylsiloxane

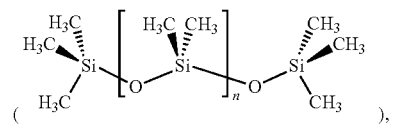

Or polycarbonate

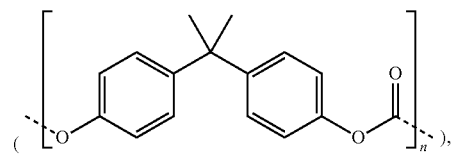

a pressure sensitive adhesive (PSA), a resin, or another photoresist.

Figure 5D:
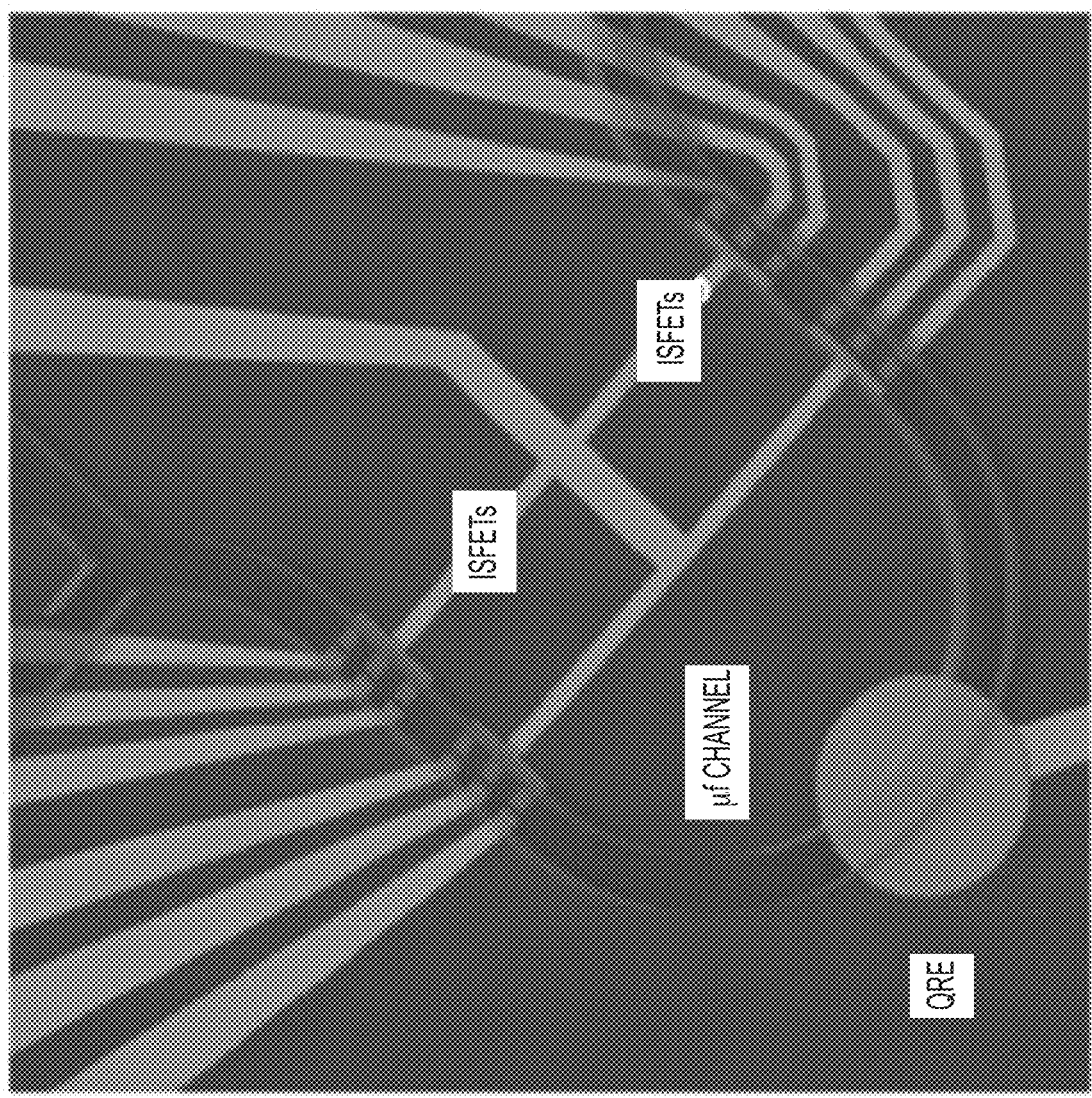
FIG. 5D is an optical micrograph of a serpentine microchannel of a biofluid collection and sensing device over a gold gate ion-sensitive field effect transistor (ISFET) and quasi-reference electrode (QRE), according to an illustrative embodiment.

Referring again to FIG. 3, the microfluidic and/or nanofluidic channels of microfluidic layer 330 are shaped and sized to facilitate the transfer of a biofluid from inlet(s) 352, through the corresponding channel, and out of the at least one outlet. For example, the geometry and size of the microfluidic and/or nanofluidic channels may be selected to provide efficient biofluid introduction (e.g., via capillary motion) using micro pump(s) 334. In certain embodiments, the microfluidic and/or nanofluidic channels have a width from 100 nm to 1000 micrometers (μm) and a height from 100 nm to 500 μm. In certain embodiments, a portion of the channels are nanofluidic channels of less than 100 nm in height. In certain embodiments, nanofluidic channels can provide desirable flow characteristics. Nanofluidic channels can also act as a filter and prevent large objects such cells (e.g., from skin desquamation) and bacteria (e.g., from skin flora) from reaching the semiconductor sensors and interfering with measurements. In certain embodiments, at least a portion of the microfluidic and/or nanofluidic channel(s) has a serpentine shape. For example, the geometry of the microfluidic and/or nanofluidic channel(s) may be selected to efficiently direct biofluid to flow through or over one or more of the semiconductor sensors 312, 314, 316, and/or 318. FIG. 5D is an optical micrograph 530 of a serpentine microfluidic channel of a biofluid collection and sensing device, according to an illustrative embodiment. The serpentine microchannel shown in FIG. 5D conveys fluid over an array of gold gate ISFETs and a QRE to facilitate biomarker sensing.

Figure 4A:
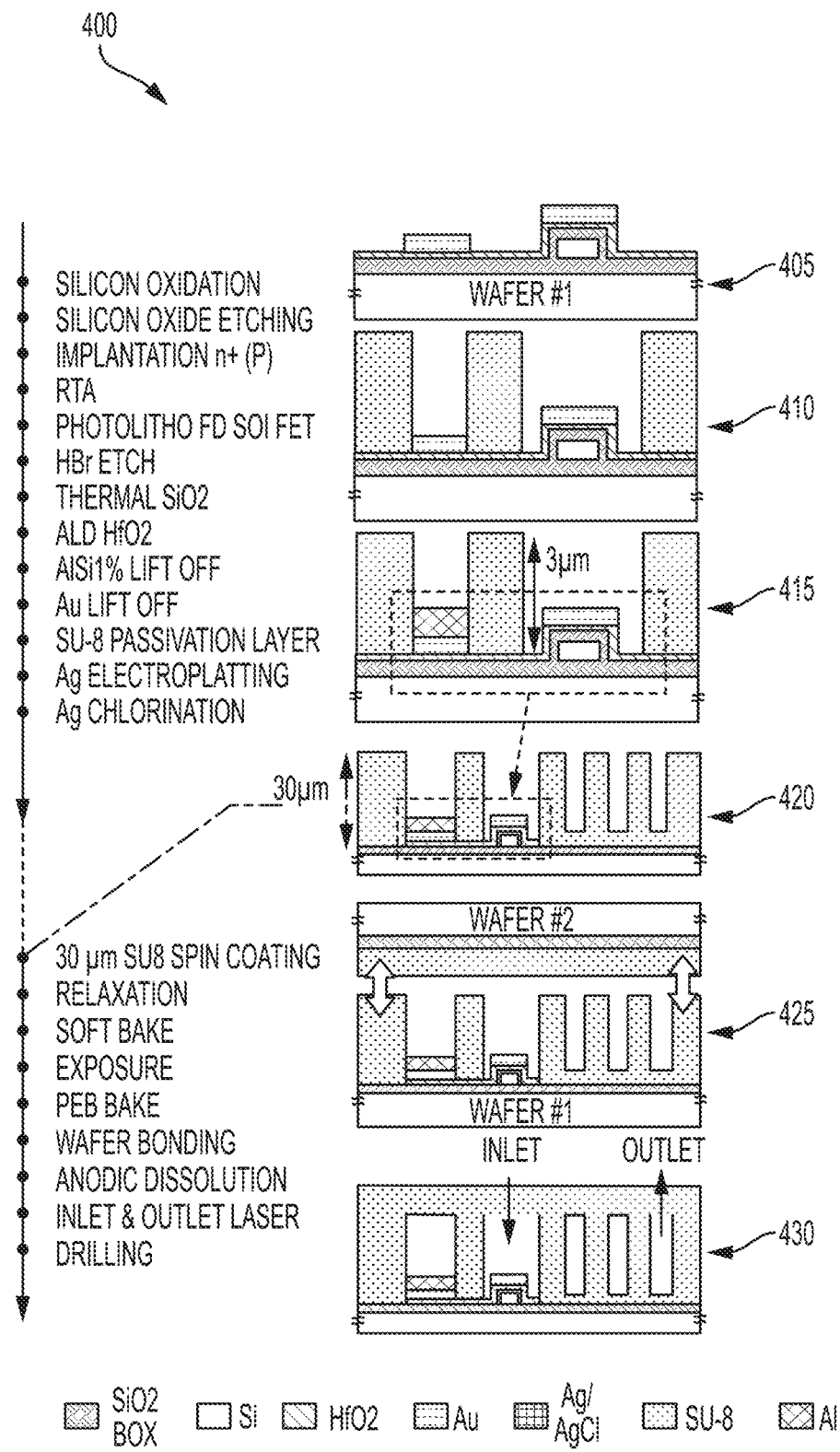
FIG. 4A is a diagram depicting the process used to fabricate a biofluid collection and sensing device, according to an illustrative embodiment.
Figure 4B:
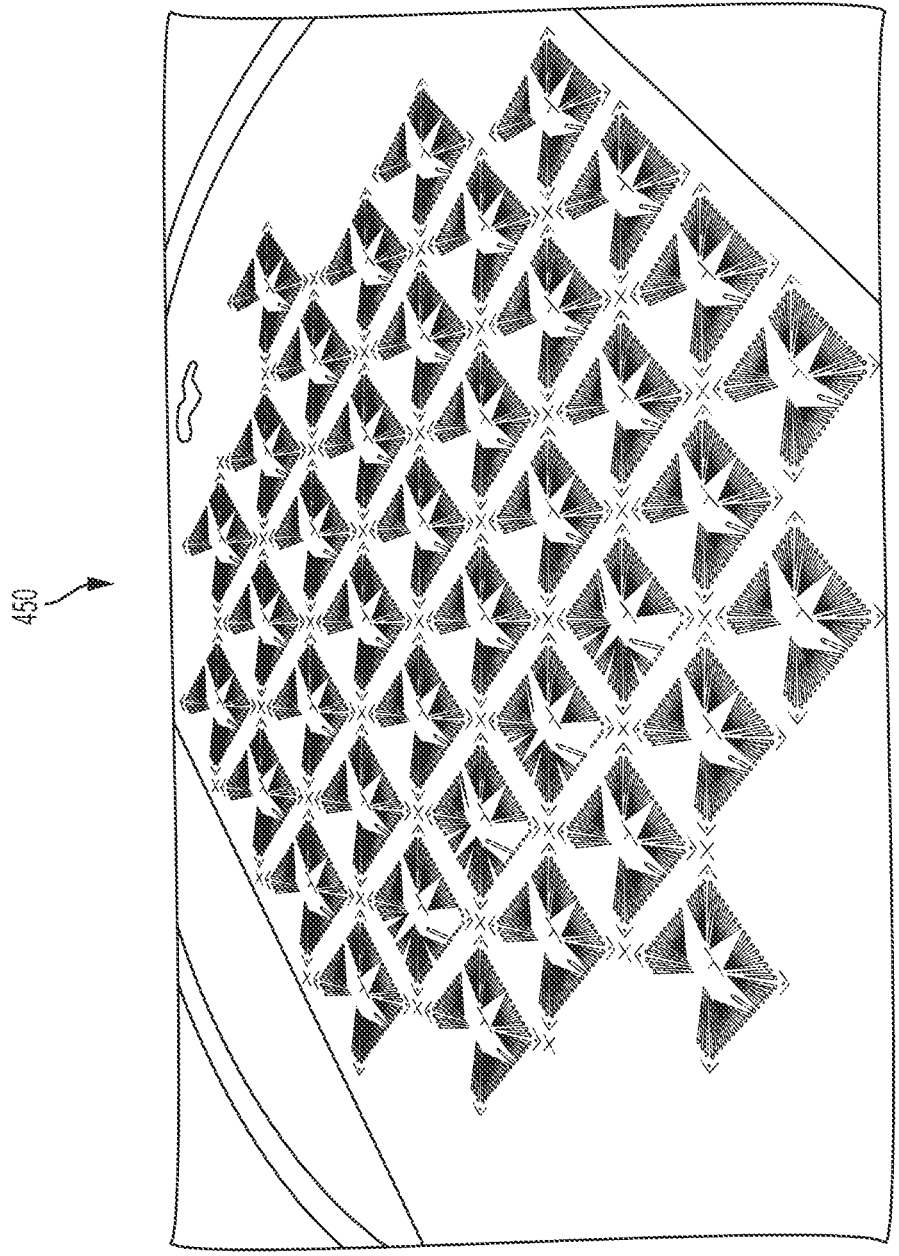
FIG. 4B is a top-view illustration of the semiconductor sensors of a biofluid collection and sensing device, according to an illustrative embodiment.
Figure 4C:
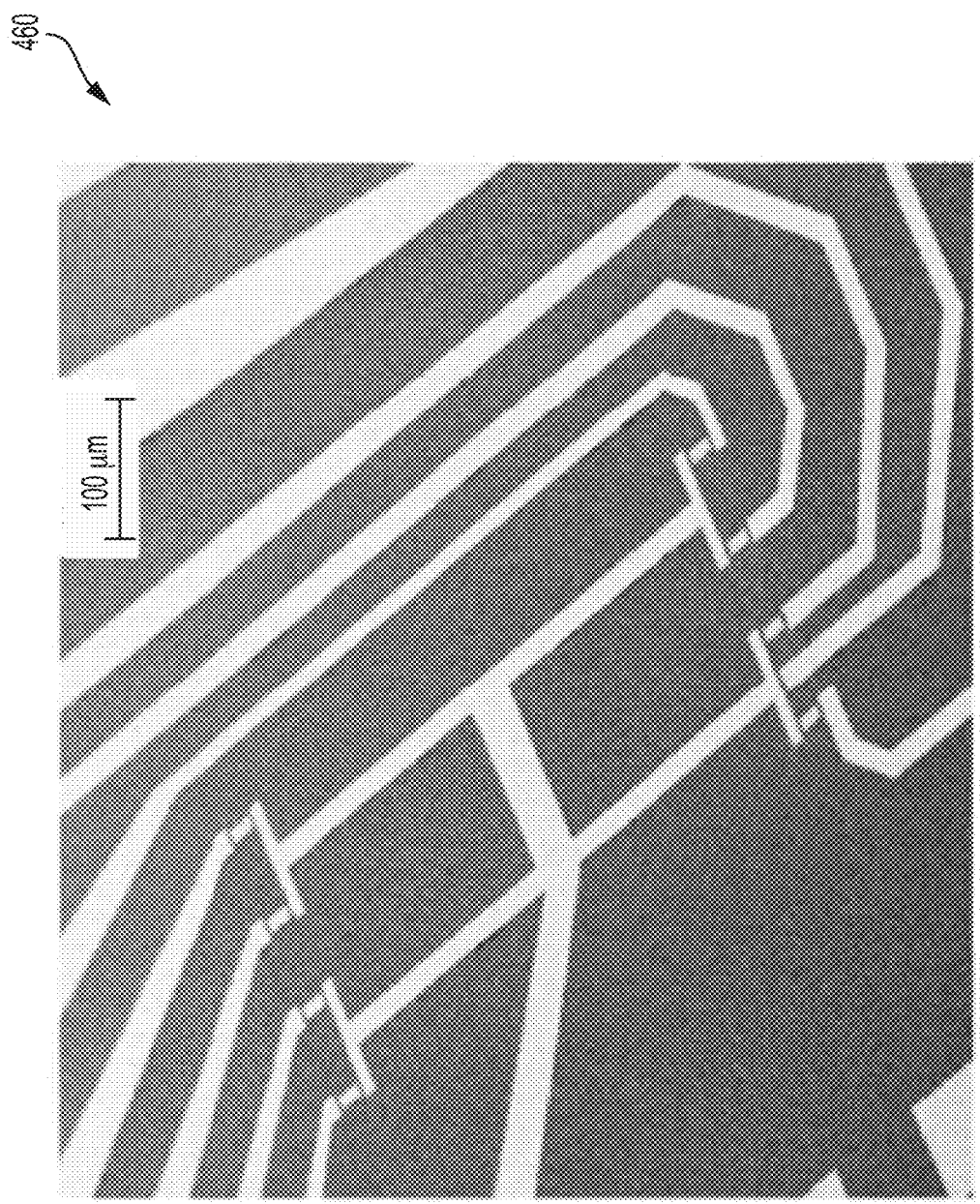
FIG. 4C is an scanning electron microscopy (SEM) micrograph of an array of semiconductor sensors of a biofluid collection and sensing device, according to an illustrative embodiment.

FIG. 4A shows an illustrative example of a process 400 for fabricating a biofluid collection and sensing device. In step 405, FET sensors are fabricated. The devices are built on an FD-SOI substrate, which provides superior electrostatic control and low leakage current compared to other substrates. The FD-FET sensors have a ribbon-like form factor, with a silicon film thickness of about 30 nm and channel widths from about 0.8 μm to about 4 μm. An about 3 nm thick layer of $HfO_2$ is deposited as the gate dielectric. $HfO_2$ provides a nearly Nernstian response to pH and ultra-low gate leakage. $HfO_2$ is deposited via atomic layer deposition (ALD) on a layer of dry thermal $SiO_2$ that has a thickness of about 2 nm. This process provides an $HfO_2$/$SiO_2$ gate stack that has an interface with very few defects. Metal lines of AlSi 1% are deposited by lift-off followed by contact annealing. The pH sensors (e.g., sensor 312 of FIG. 3) have no metallization on the high-k gate stack. For the functionalized sensors (e.g., sensors 316 and 318 of FIG. 3) and the control sensor (e.g., sensor 314 of FIG. 3), a layer of gold about 100 nm thick is sputtered on top of the gate stacks. FIG. 4C shows an SEM micrograph 460 of an illustrative embodiment of the semiconductor sensors of a sensing device as described herein.

In step 410, surfaces are passivated with SU-8 to isolate the FET sensors from the interconnects. The SU-8 passivation layer is about 3 μm thick. There are only openings in the passivation layer in the sensor channel regions and in areas used to make electrical contact (e.g., at contact pads).

In step 415, a quasi-reference electrode (QRE) is, optionally, fabricated. The wafer is first passivated with a photoresist, and only a portion of the gold layer pattern is exposed (e.g., without photoresist) for the creation of QRE(s). An about 3 μm thick layer of silver (Ag) is electroplated on top of the exposed gold and is chlorinated to obtain a miniaturized QRE with a thickness of about 3.6 μm.

In step 420, a first microfluidic layer is fabricated that includes channels and micro pumps. A biocompatible layer of SU-8 (about 30 μm thick) is processed on top of the SOI wafer with passivated FET sensors. This layer is patterned using photolithography techniques to form the channels and micro pumps of the first microfluidic layer. Deposition and baking times of the SU-8 are optimized to achieve the desired aspect ratios.

In step 425, the first microfluidic layer is bonded to a second microfluidic layer (e.g., a "lid" layer). In order to close the channels, a second wafer is coated with SU-8 and processed. A layer of aluminum (Al) about 500 nm thick is first sputtered on the wafer. An about 30 μm thick layer of SU-8 is then coated on the Al. In certain embodiments, the second microfluidic layer can include additional microfluidic structures (e.g., channels, pillars, and the like). A post exposure bake is performed at 90° C. before the wafers are contacted together under a pressure of 4 bars at 120° C. This step ensures that the two microfluidic layers are securely bonded and the channels are closed.

In step 430, anodic dissolution is performed to dissolve the Al layer and release the second wafer (used in the second microfluidic layer). During anodic dissolution, the bonded wafers are placed in a 1 M NaCl solution and 5 volts (V) is applied to achieve anodic dissolution of Al. Finally, arrays of inlets and outlets with diameters of about 90 μm diameters are drilled with an excimer laser.

In certain embodiments, the semiconductor sensors and the microfluidic channels are fabricated on different substrates. For example, a first semiconductor or semiconductor-on-insulator (SOI) (e.g., FD-SOI) substrate layer can contain the sensors, while the microfluidic or nanofluidic channels are formed from a second substrate layer (e.g., with two or more integrated microfluidic layers). The first and second substrates are then connected to form an integrated biofluid collection and sensing device. In other embodiments, the semiconductor sensors and the microfluidic or nanofluidic channels are fabricated on the same semiconductor or semiconductor-on-insulator (SOI) (e.g., FD-SOI) substrate layer.

Figure 22:
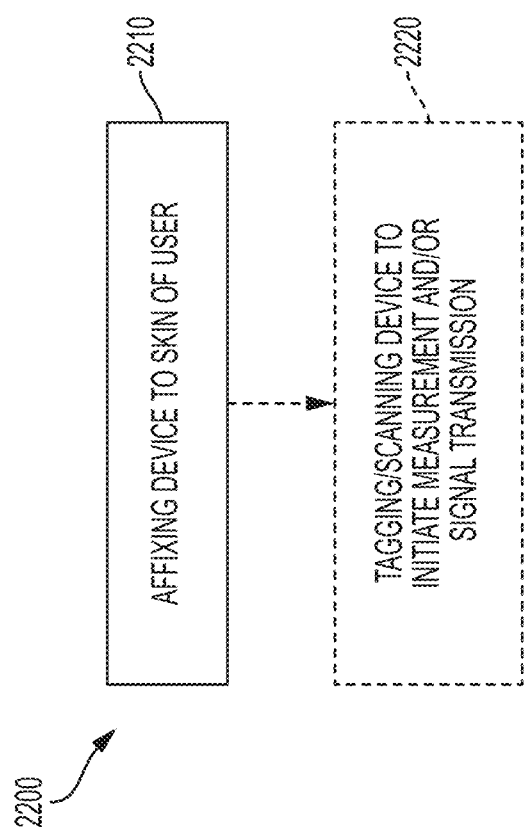
FIG. 22 is a block flow diagram of a method for using a biofluid collection and sensing device, according to an illustrative embodiment.

FIG. 22 shows a block flow diagram of a method 2200 of using a biofluid (e.g., sweat, e.g., human sweat) collection and sensing device (e.g., wearable device). In step 2210, the biofluid collection and sensing device, described herein, is affixed to a human body (e.g., the skin of a user. The device can be affixed via a fixture module (e.g., an adhesive patch as the illustrative example of shown in FIG. 1) or placed in contact with the skin via another wearable apparatus (e.g., a watch or wrist band as shown in the illustrative example of FIG. 2). The interface and/or the interface surface of the biofluid collection and sensing device is in contact with a surface (e.g., skin) of the human body.

In certain embodiments, the device can be tagged (e.g., scanned) (e.g., before or after being affixed to the human body) with a mobile device [e.g., with the camera or with a wireless communication module (e.g. a Near Field Communications (NFC) module, e.g., a Wi-Fi module, e.g., a Bluetooth® module) of a mobile phone device] to initiate measurements and/or facilitate communication between the biofluid collection and sensing device and the mobile device (step 2220). For example, the biofluid collection and sensing device may include a barcode that can be scanned by a mobile device. For example, the step of tagging (step 2210) can trigger the biofluid collection and sensing device to begin collecting and sensing the biofluid.

The step of tagging (step 2210) can trigger the biofluid collection and sensing device to initiate signal transmission (e.g., wireless electronic signal transmission) from the biofluid collection and sensing device to the mobile device. In this way, the user can control when the biofluid collection and sensing device begins measuring and can determine where the measurement data will be sent (e.g., to the mobile device or another computing device). The transmitted measurement data can be sent to the mobile device (e.g., or other computing device) in real time or, for example, in response to a user's request to "sync" with the biofluid collection and sensing device.

Figure 23:
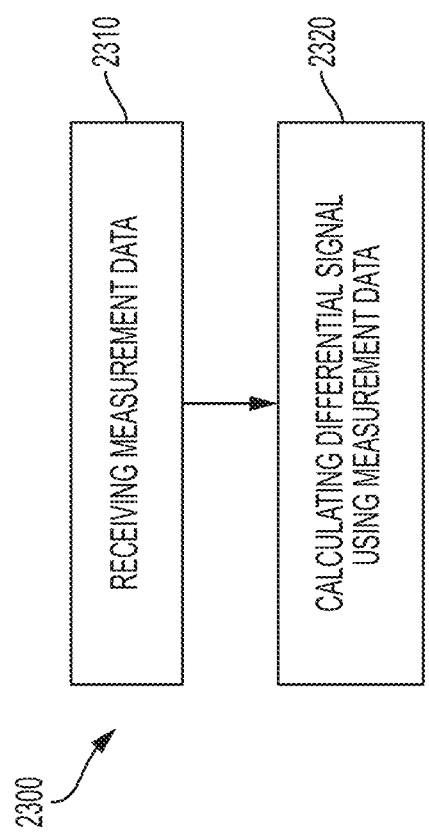
FIG. 23 is a block flow diagram of a method for sensing one or more biomarkers in a biofluid using a biofluid collection and sensing device by calculating a differential measurement signal, according to an illustrative embodiment.

FIG. 23 shows a block diagram of a method 2300 for sensing (e.g., the presence and/or quantity of) one or more biomarkers in a biofluid using a biofluid collection and sensing device. Method 2300 allows measurements to be performed using a differential signal calculated from the signal from two sensor types, e.g., a functionalized semiconductor sensor (e.g., sensor 318 of FIG. 3) and a control sensor (e.g., sensor 314 of FIG. 3). This approach can improve measurement selectivity, sensitivity, and repeatability by effectively accounting for unwanted signal (e.g., background signal) that is not associated with the analyte of interest for a given functionalized sensor.

In step 2310, data from a biofluid collection and sensing device is received (e.g., continuously), by a processor of a computing device (e.g., an analysis module of a biofluid collection and sensing device, e.g., a mobile device). The data includes at least a signal a control signal from control sensor and a biomarker signal from a functionalized sensor. For example, the control sensor may be an FD-FET with an un-functionalized gate, while the functionalized sensor is an FD-FET with a functionalized gate (e.g., functionalized with selective moieties such as a plurality of crown ether molecules).

In step 2320, a differential biomarker signal is calculated (e.g., continuously) using the control signal and the biomarker signal. For example, the differential signal can be the difference between the control signal and the biomarker signal, the ratio of the control signal and the biomarker signal, or another mathematical function applied to the two signals.

EXPERIMENTAL EXAMPLES

Example 1

Measuring pH

Figure 8:
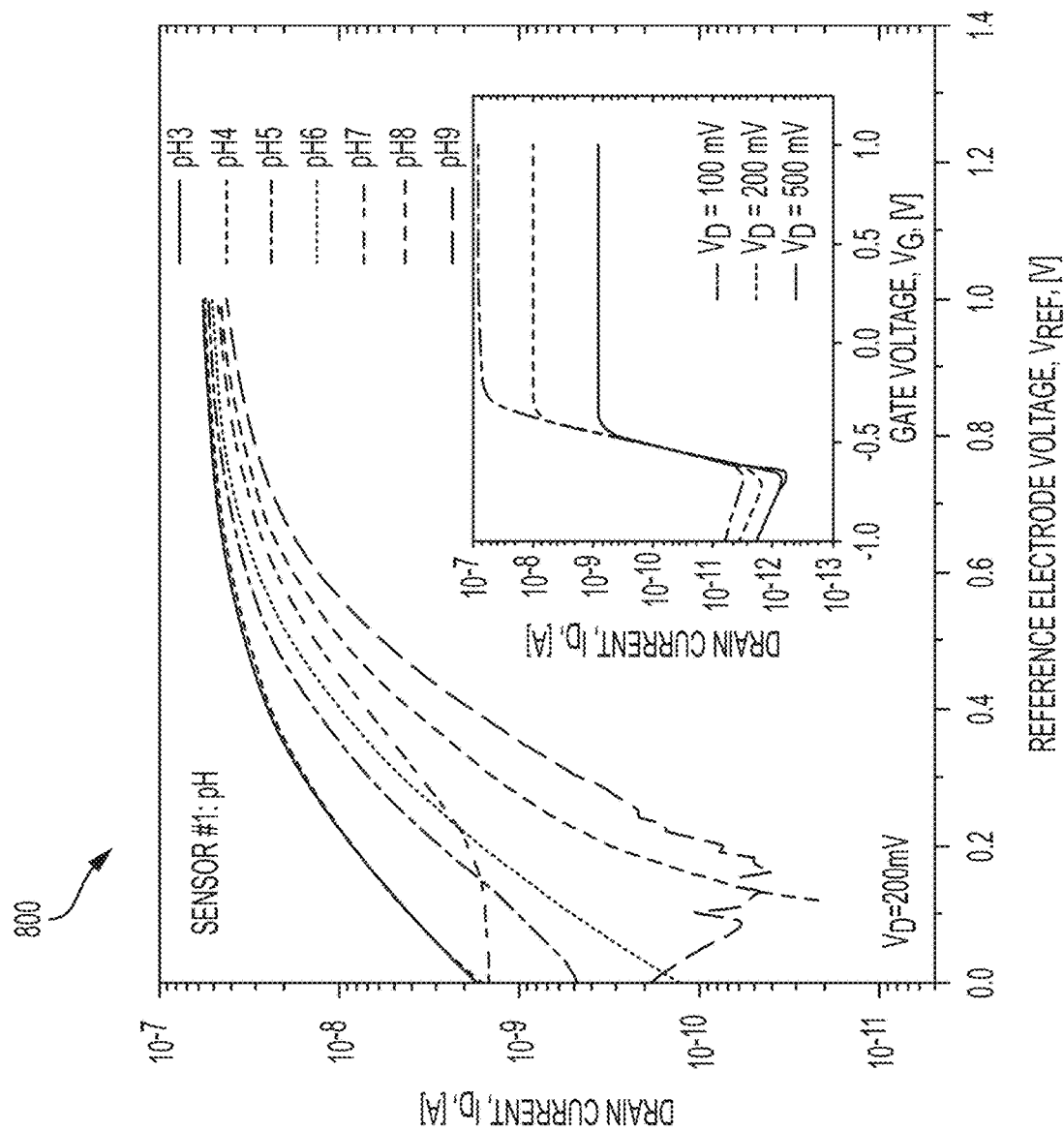
FIG. 8 is a plot of drain current versus gate voltage (e.g., $I_D$-$V_G$) for a pH sensor with an $HfO_2$ gate at various pH values, according to an illustrative embodiment.
Figure 9:
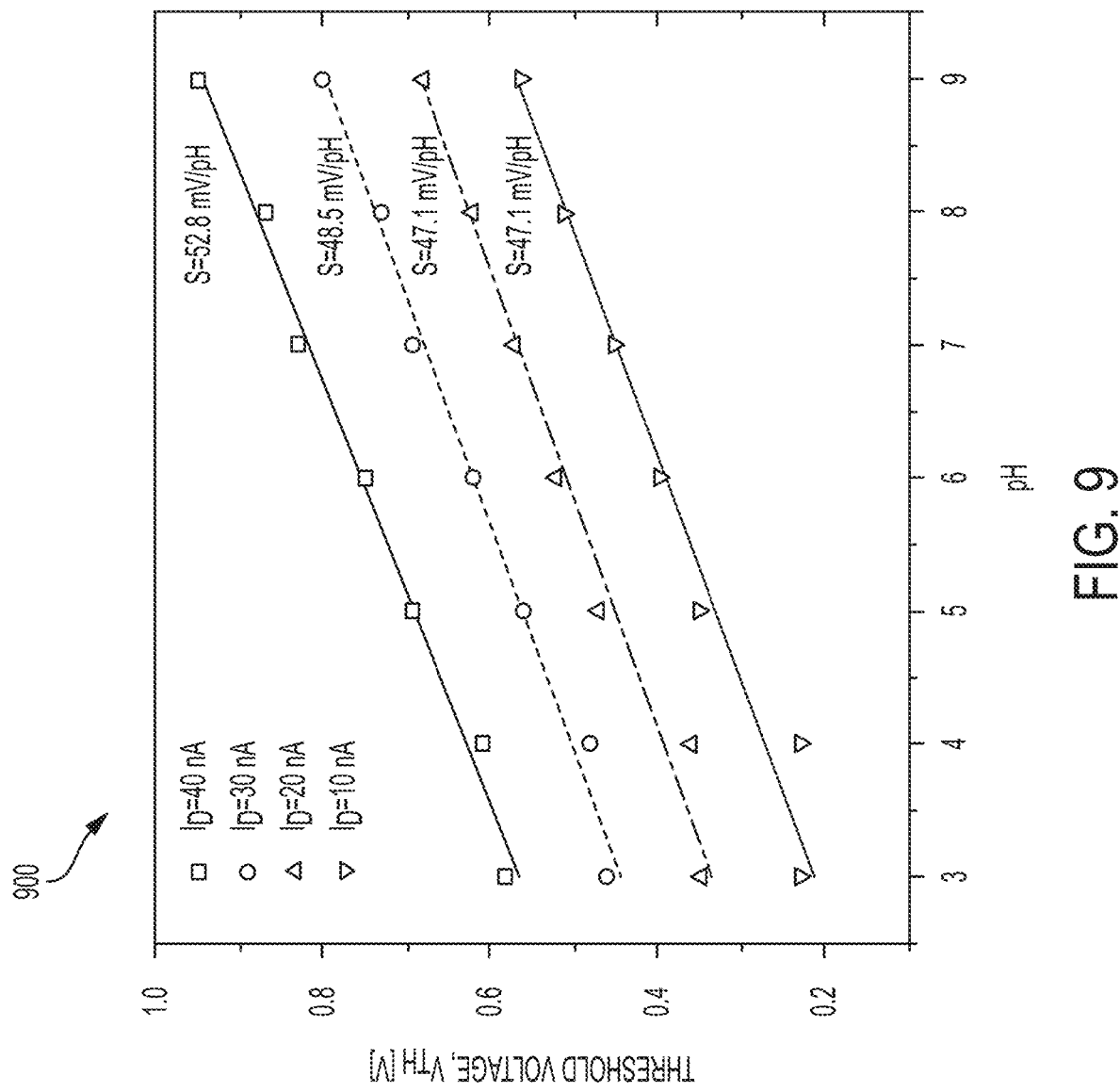
FIG. 9 is a plot of threshold voltage versus pH at different drain current ($I_D$) levels, according to an illustrative embodiment.

A bio-fluid collection and sensing device was prepared with a $HfO_2$ gate (sensor #1) as a pH sensor. In order to characterize the pH response of sensor #1, sensor #1 was exposed to buffers with pH values from pH 3 to 9, and the $I_D$-$V_G$ characteristics of sensor #1 were measured at each pH, as shown in plot 800 of FIG. 8. To evaluate the pH sensitivity of sensor #1, threshold voltages were extracted from the $I_D$-$V_G$ characteristics shown in FIG. 8. FIG. 9 shows a plot 900 of these extracted threshold voltages versus pH at various drain current levels from 10 nA to 40 nA, corresponding to weak inversion conditions. As shown in FIG. 9, a full scale sensitivity of 52.8 mV/pH was obtained for sensor #1 at a constant drain current of 40 nA. For comparison, the inset to FIG. 8 shows the $I_D$-$V_G$ characteristics of a conventional FD SOI FET with a metal gate which displayed a quasi-ideal subthreshold swing (SS) of 62 mV/dec and an ultralow off-state current (i.e., $I_{off}$).

Figure 10:
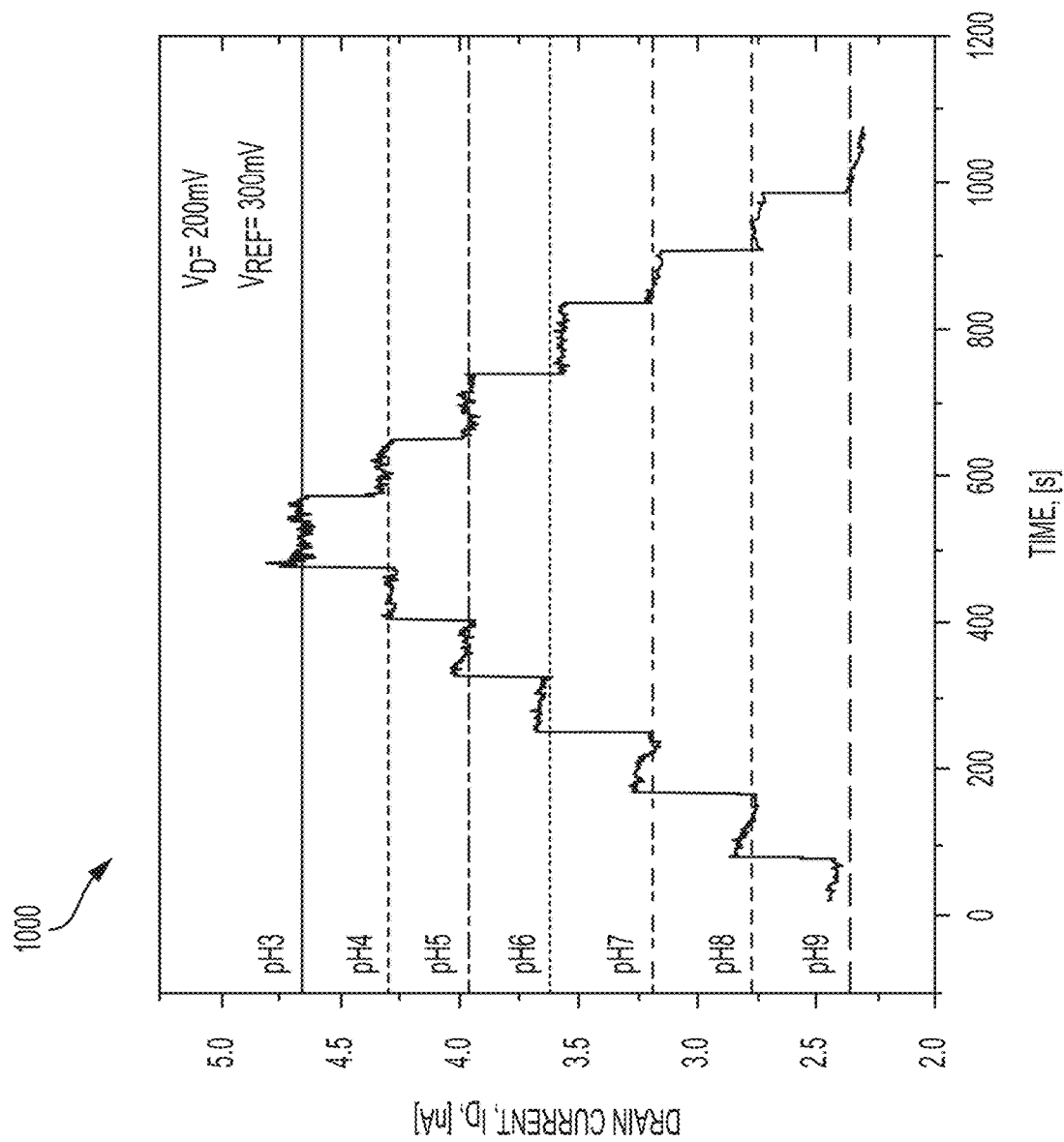
FIG. 10 is a plot of the dynamic measurement of drain current ($I_D$) versus time for a pH sensor with a bare $HfO_2$ gate at various pH values, according to an illustrative embodiment.

Dynamic pH measurement were then performed to characterize the dynamic response of sensor #1 by perfusing buffers with various pH values from pH 3 to 9 through a microfluidic channel of the bio-fluid collection and sensing device. Sensor #1 was first exposed to a pH 9 buffer. The pH of the buffer was then decreased step-wise every 100 s until reaching pH 3 before being increased in the same step-wise fashion back to pH 9. FIG. 10 shows a plot 1000 of the drain current ($I_D$) versus time for sensor #1 during these dynamic changes in microchannel pH. As shown in FIG. 10, sensor #1 was highly stable and had a time response of less than 5 s.

Example 2

Measuring Na+ from the Differential Response of a Control Sensor and a Na+-Selective Sensor A control sensor was prepared with a non-functionalized gold gate (sensor #2), and a $Na^+$ sensor was prepared with a hydroxyl crown ether-functionalized gold gate (sensor #3).

Figure 11:
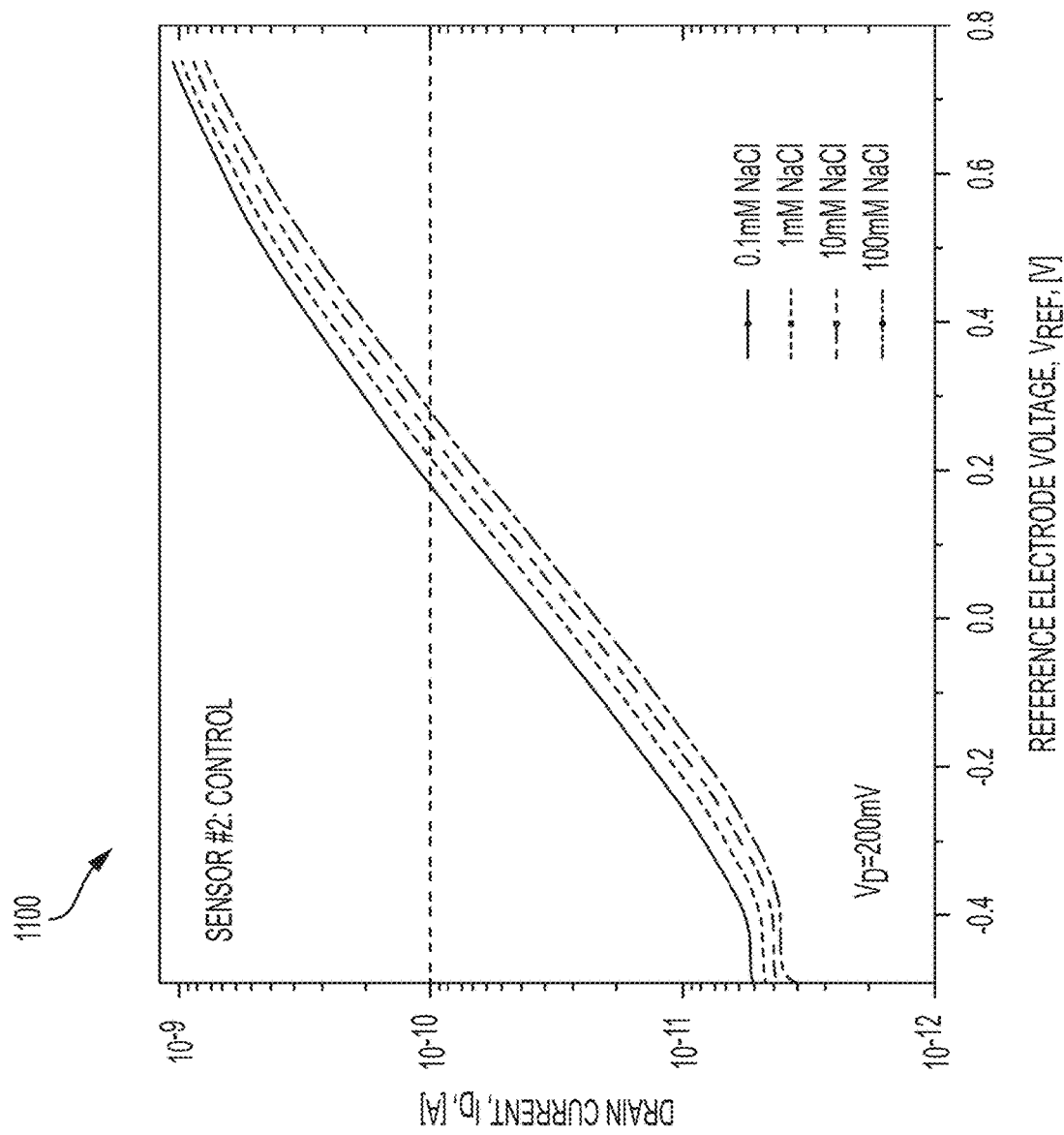
FIG. 11 is a plot of drain current versus gate voltage (e.g., $I_D$-$V_G$) for a non-functionalized (e.g., control) sensor at various concentrations of NaCl, according to an illustrative embodiment.
Figure 12:
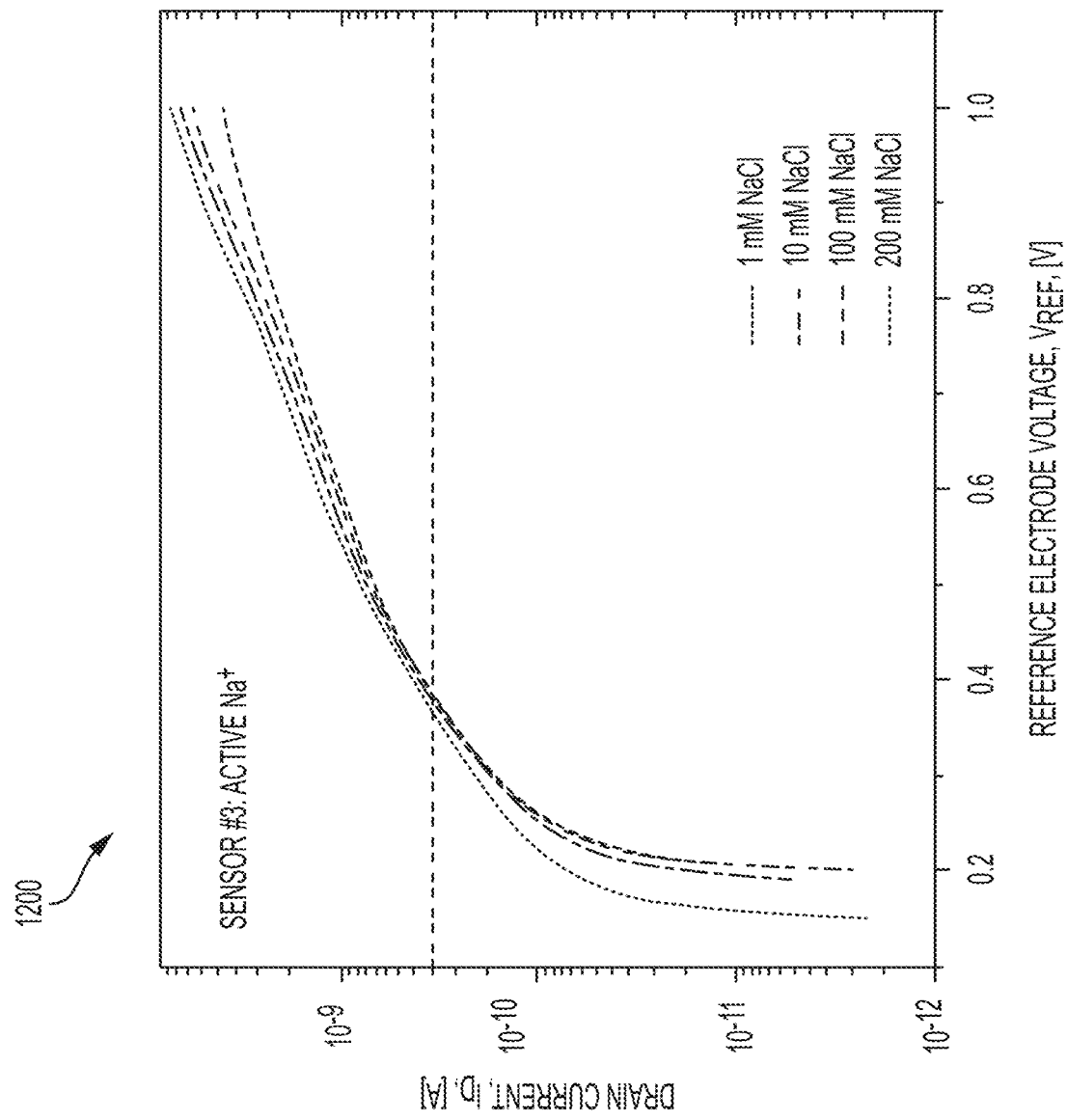
FIG. 12 a plot of drain current versus gate voltage (e.g., $I_D$-$V_G$) for a sensor functionalized for $Na^+$ sensing with a 15-crown hydroxyl crown ether at various concentrations of NaCl, according to an illustrative embodiment.
Figure 13:
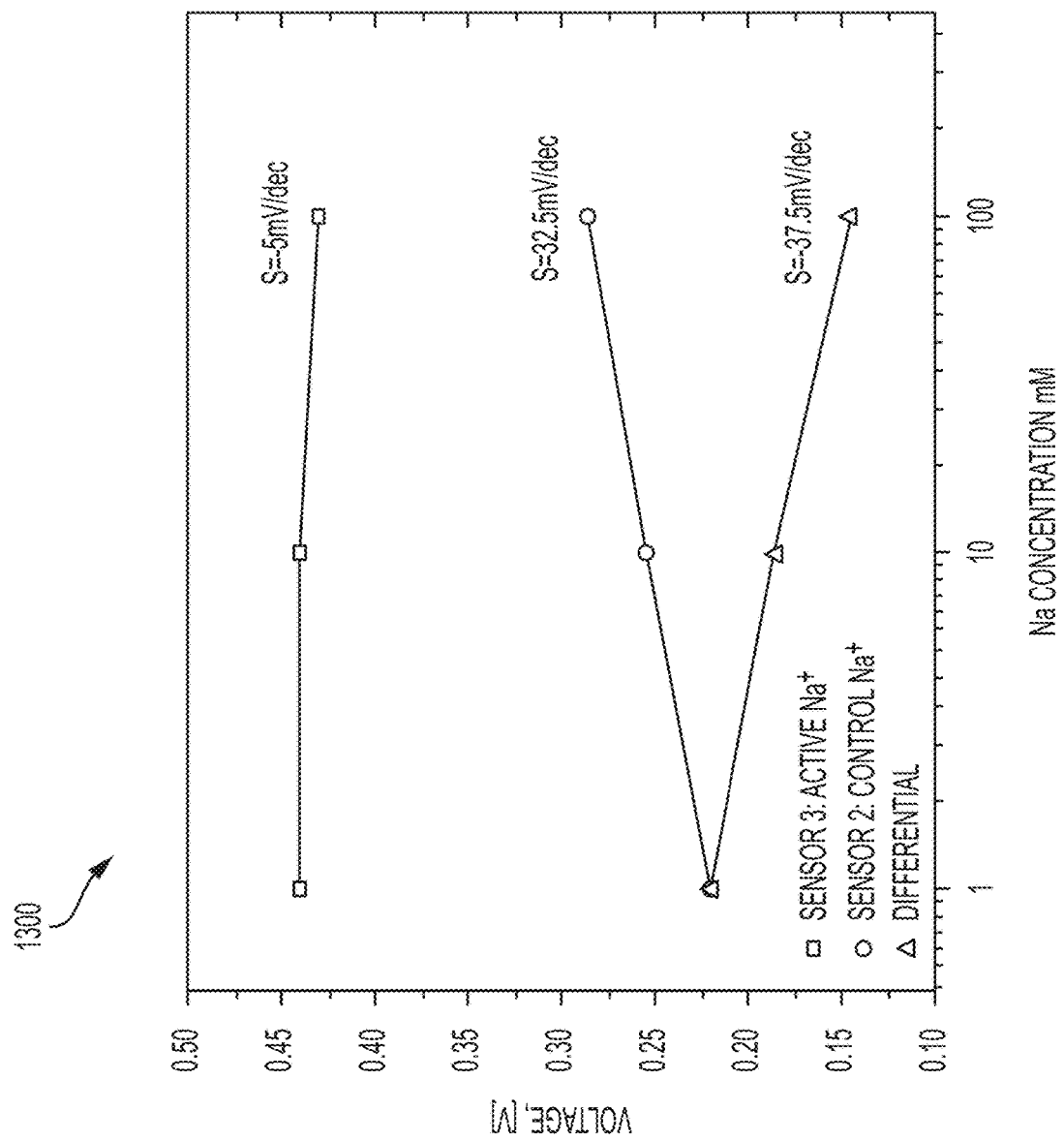
FIG. 13 is a plot of voltage versus $Na^+$ concentration for a non-functionalized (e.g., control) sensor and a $Na^+$ sensor functionalized for $Na^+$ sensing with a 15-crown hydroxyl crown ether and a plot of the differential signal derived from both sensors, according to an illustrative embodiment.

In order to characterize the responses of sensor #2 and sensor #3 to $Na^+$, each sensor was exposed to an electrolyte containing NaCl at a concentration from 0.1 mM to 100 mM. The $I_D$-$V_G$ characteristics of each sensor were then measured at each NaCl concentration, as shown in plot 1100 of FIG. 11 for sensor #2 and plot 1200 of FIG. 12 for sensor #3. Threshold voltages were then extracted for each sensor, as shown in plot 1300 of FIG. 13. Sensor #2 displayed a full scale sensitivity to $Na^+$ of 32.5 mV/dec, and sensor #3 displayed a full scale sensitivity to $Na^+$ of −5 mV/dec. A differential $Na^+$ measurement was obtained by subtracting the threshold voltages of sensor #2 from the threshold voltages of sensor #3, as shown in FIG. 13. The "differential selective sensitivity" obtained from this differential $Na^+$ measurement was −37.5 mV/dec.

Figure 14:
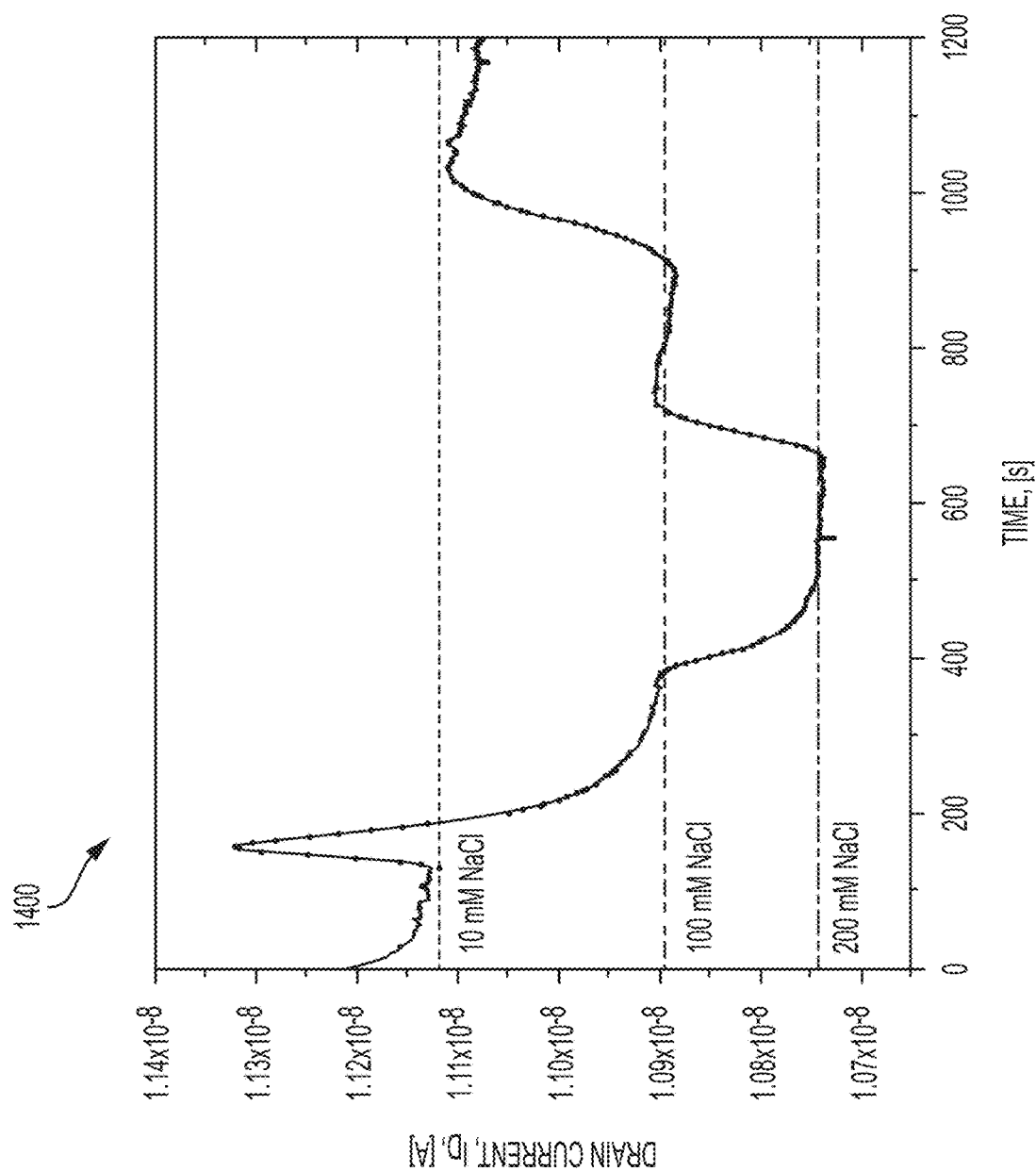
FIG. 14 is a plot of differential drain current ($I_D$) versus time for measurements with a $Na^+$ sensor and a control sensor at various concentrations of NaCl, according to an illustrative embodiment.

Dynamic measurements of $Na^+$ were then performed to characterize the dynamic differential response of sensor #3 and sensor #2 by perfusing a microfluidic channel of the bio-fluid collection and sensing device with electrolytes containing different concentrations of NaCl. FIG. 14 shows a plot 1400 of the drain current versus time for the differential measurements obtained from sensor #3 and sensor #2 at NaCl concentrations of 10, 100, and 200 mM. As shown in FIG. 14, the differential $Na^+$ measurement from sensor #3 and sensor #2 was reproducible at each NaCl concentration.

Example 3

The Differential Response of a Control Sensor and a Na+-Selective Sensor is Affected by pH The pH responses of sensor #2 and sensor #3 were determined to evaluate the ion selectivity (e.g., the selectivity for $Na^+$ versus pH) of the differential Na+ measurements described above.

Figure 15:
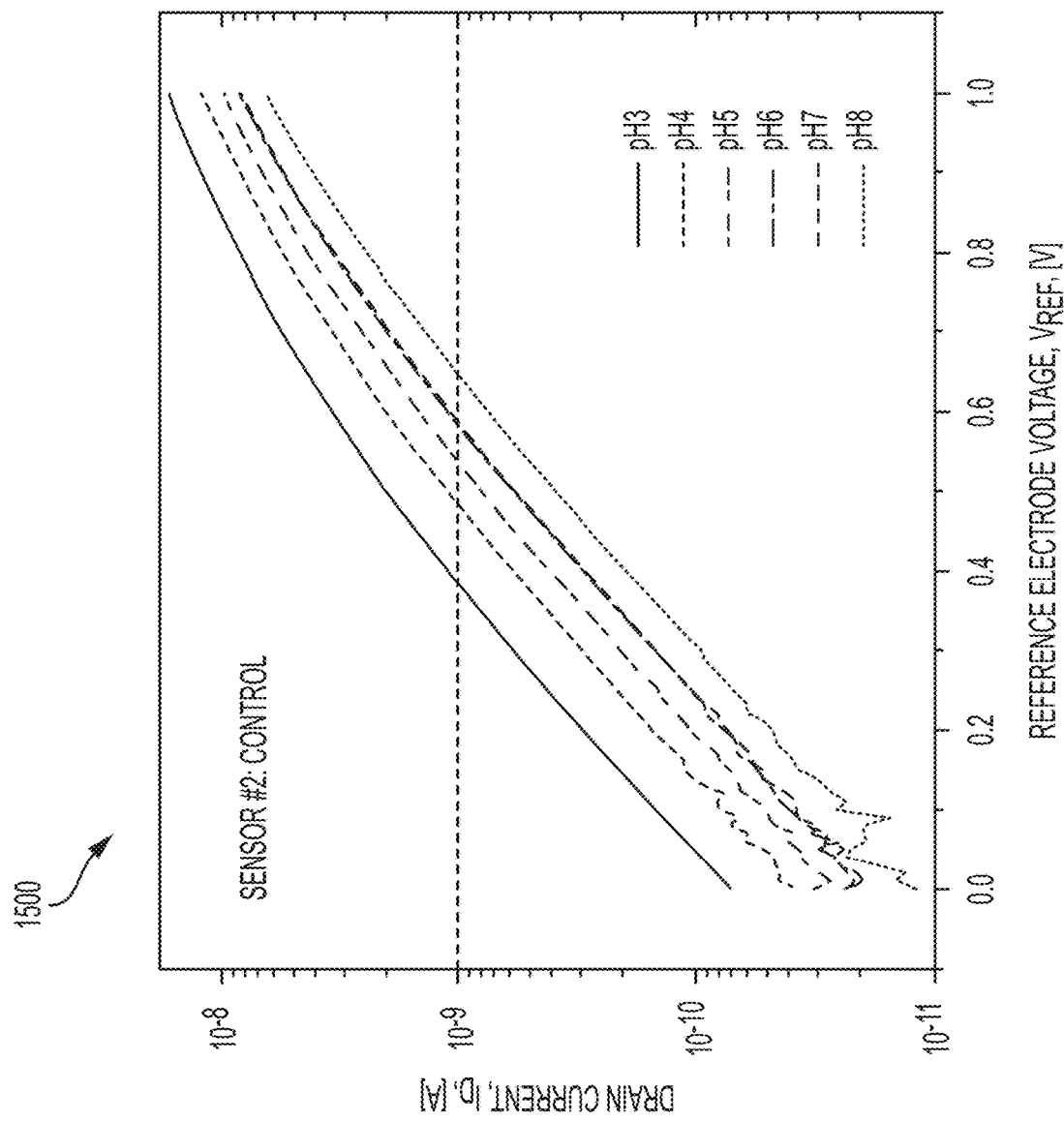
FIG. 15 is a plot of drain current versus gate voltage (e.g., $I_D$-$V_G$) for a non-functionalized (e.g., control) sensor at various pH values, according to an illustrative embodiment.
Figure 16:
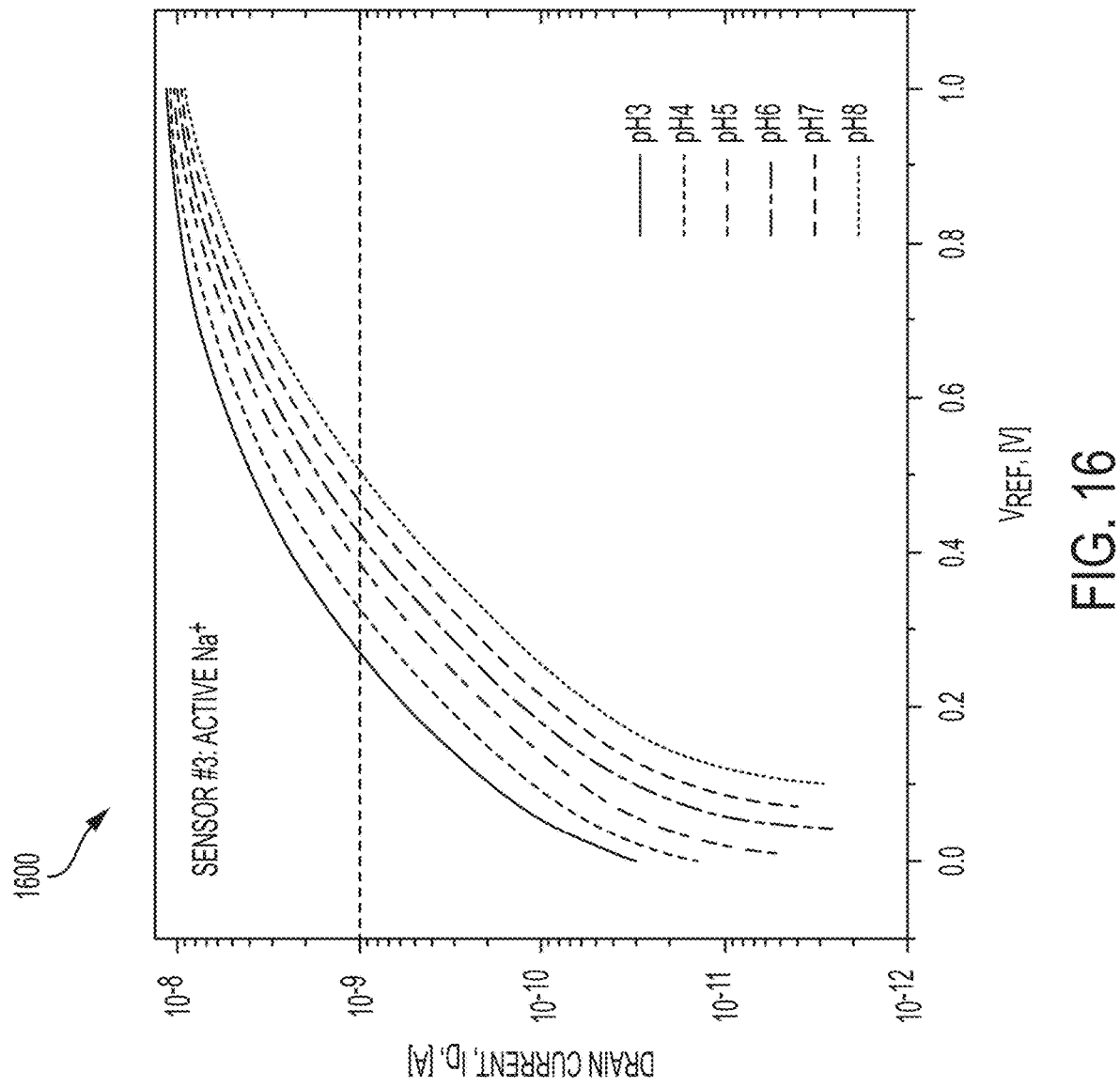
FIG. 16 is a plot of drain current versus gate voltage (e.g., $I_D$-$V_G$) for a $Na^+$ sensor functionalized for $Na^+$ sensing with a 15-crown ether at various pH values, according to an illustrative embodiment.
Figure 17:
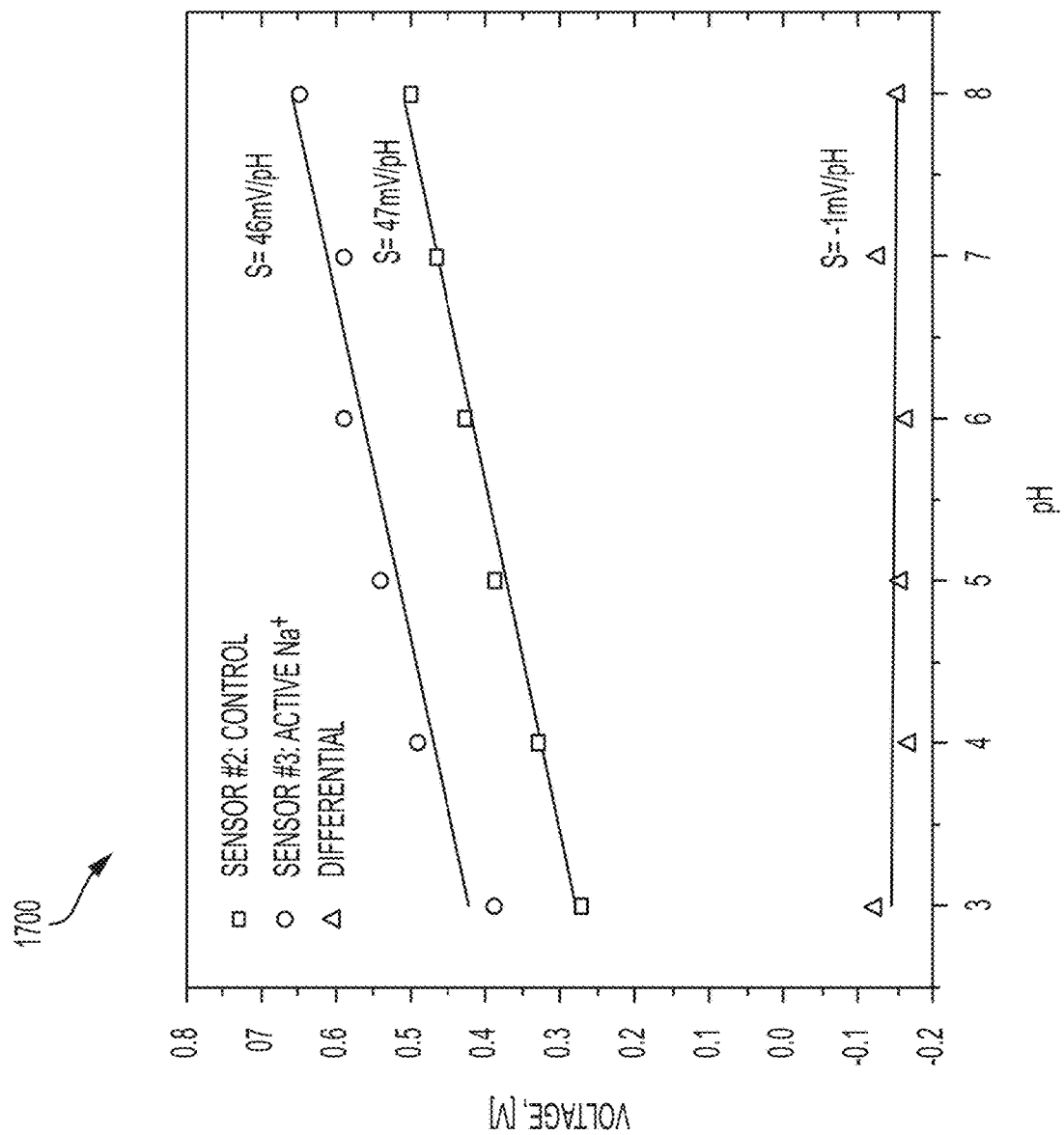
FIG. 17 is a plot of voltage versus pH for a non-functionalized (e.g., control) sensor and a $Na^+$ sensor functionalized for $Na^+$ sensing with a 15-crown ether and a plot of the differential voltage of both sensors, according to an illustrative embodiment.

In order to characterize the responses of sensor #2 and sensor #3 to pH, each sensor was exposed to buffers with different pH values from pH 3 to 9 (similarly to the approach described with respect to FIG. 8). The $I_D$-$V_G$ characteristics of each sensor were then measured at each pH, as shown in plot 1500 of FIG. 15 for sensor #2 and plot 1600 of FIG. 16 for sensor #3. These figures present the cross-sensitivity of each sensor to pH (e.g., rather than to their target ion). Threshold voltages were then extracted for each sensor, as shown in FIG. 17. Sensor #2 displayed a full scale sensitivity to pH of 47 mV/pH, and sensor #3 displayed a full scale sensitivity to pH of 46 mV/dec. A differential pH measurement was obtained by subtracting the threshold voltages of sensor #2 from the threshold voltages of sensor #3. As shown in plot 1700 of FIG. 17, this differential pH measurement (with a differential sensitivity of −1 mV/pH) was low such that the differential measurement is not significantly affected by changes in pH. The insensitivity of the differential measurement to pH indicates that the bio-fluid collection and sensing device is useful for simultaneous multi-sensing applications, e.g., in which pH and Na+ are measured at the same time.

Example 4

Measuring K+ with a K+-Selective Sensor

Figure 18:
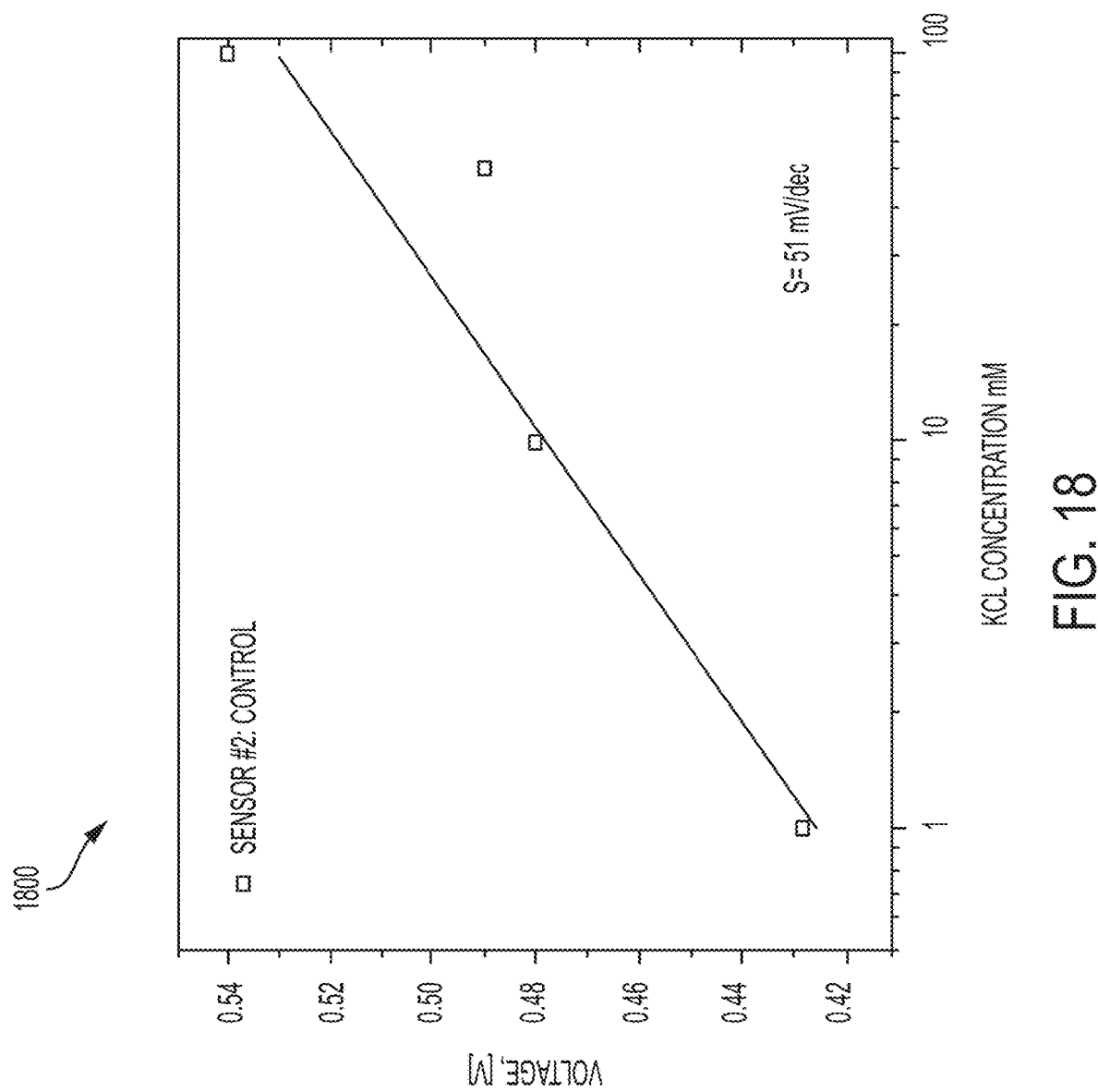
FIG. 18 is a plot of voltage versus KCl concentration for a non-functionalized (e.g., control) sensor, according to an illustrative embodiment.

FIG. 18 shows a plot 1800 of the response of sensor #2 to changes in the concentration of $K^+$. Sensor #2 displayed a $K^+$ sensitivity of 51 mV/dec, indicating that this sensor can be used for the determination of K$^+$ concentration in a bio-fluid collection and sensing device.

Example 5

Stability of the QRE

Figure 19:
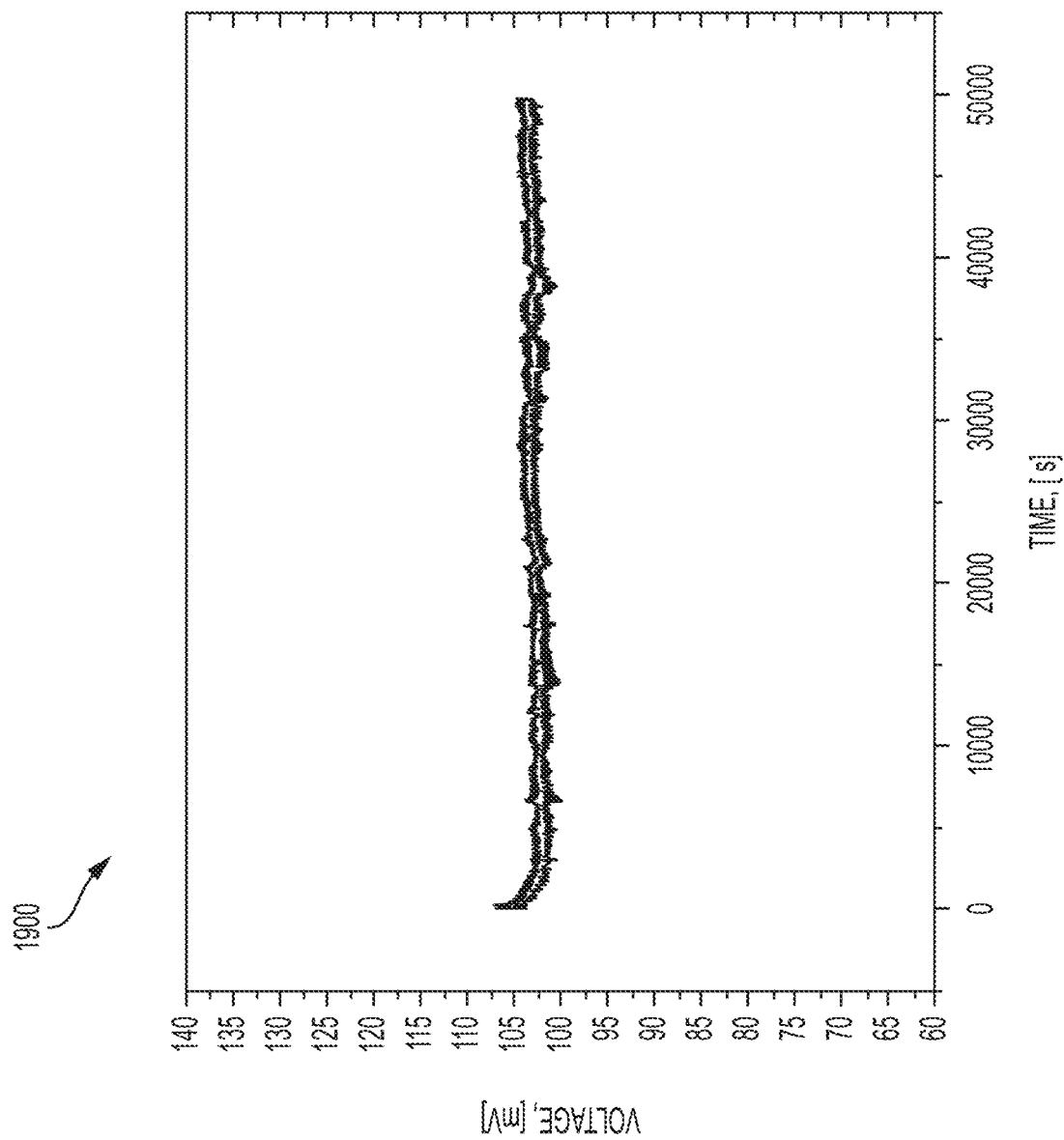
FIG. 19 is a plot of the open circuit potential (vs. the potential of a commercial flow-through AgCl reference electrode) of a Ag/AgCl QRE versus time measured in a biofluid collection and sensing device during the perfusion of a fluid containing 23 mM NaCl at 25 nanoliters (nL)/min, according to an illustrative embodiment.

The integrated Ag/AgCl QRE was coated with a polyvinyl butyral/NaCl matrix. The stability of the QRE was evaluated by measuring the open circuit potential of the QRE vs. a commercial flow-through Ag/AgCl reference electrode. Measurements were performed while a microchannel of the bio-fluid collection and sensing device was perfused with 23 mM NaCl solution at 25 nL/min. FIG. 19 shows a plot 1900 of the open circuit potential of the integrated Ag/AgCl QRE versus time. The integrated Ag/AgCl QRE remained fully stable for at least 50,000 s (about 14 hours), ensuring long-term stability of the QRE during operation (e.g., for hours, e.g., for days, e.g., for weeks).

Computer and Network Implementation

Figure 20:
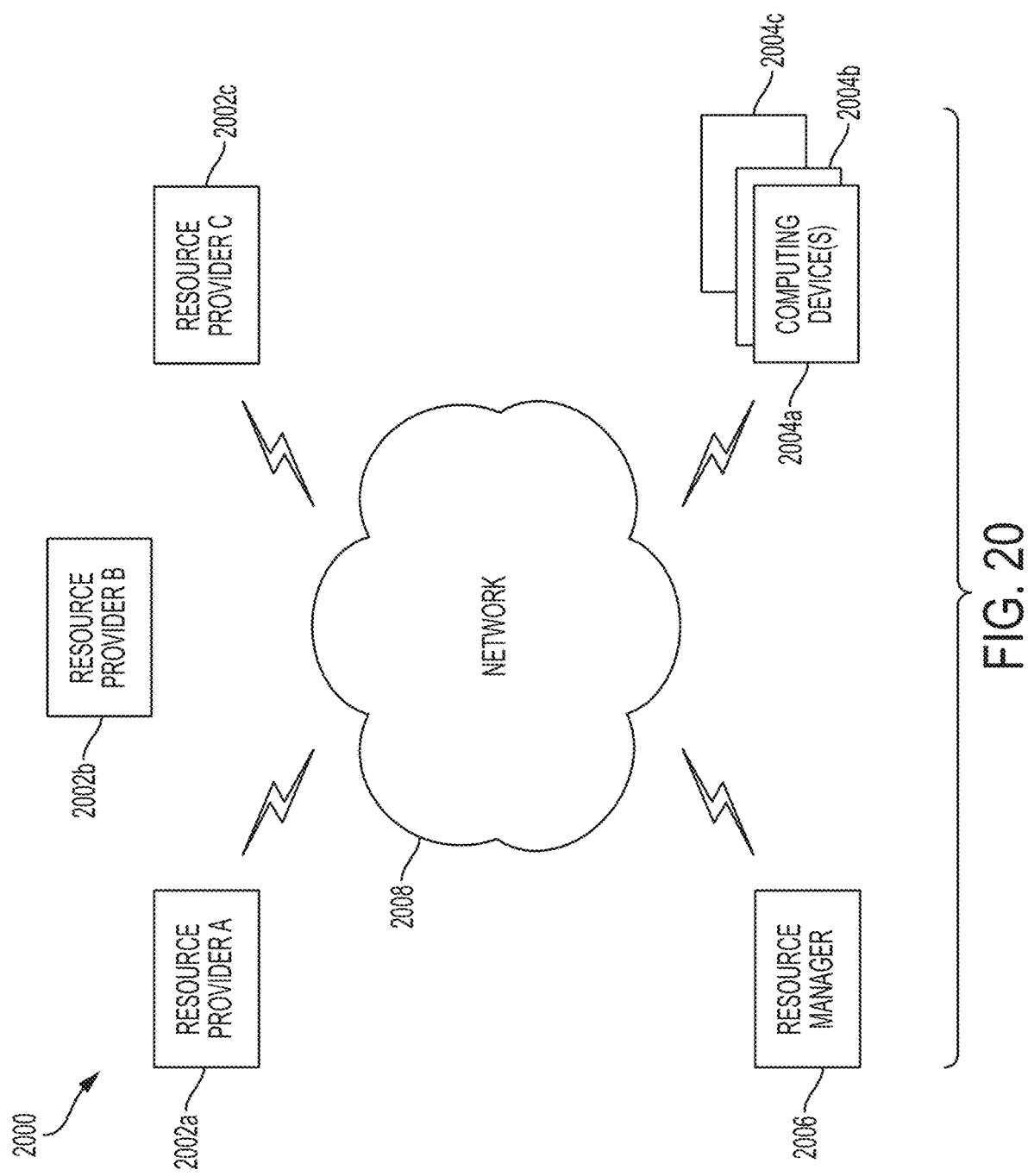
FIG. 20 depicts a block diagram of an exemplary cloud computing environment, used in certain embodiments of the biofluid collection and sensing device described herein.

As shown in FIG. 20, an implementation of a network environment 2000 which may be used in certain embodiments described herein, is shown and described. For example, data from the wearable sensing device may be transmitted to and/or otherwise acquired by a remote device for processing, result determination, result display, or the like. In brief overview, referring now to FIG. 20, a block diagram of an exemplary cloud computing environment 2000 is shown and described. The cloud computing environment 2000 may include one or more resource providers 2002a, 2002b, 2002c (collectively, 2002). Each resource provider 2002 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 2002 may be connected to any other resource provider 2002 in the cloud computing environment 2000. In some implementations, the resource providers 2002 may be connected over a computer network 2008. Each resource provider 2002 may be connected to one or more computing device 2004a, 2004b, 2004c (collectively, 2004), over the computer network 2008.

The cloud computing environment 2000 may include a resource manager 2006. The resource manager 2006 may be connected to the resource providers 2002 and the computing devices 2004 over the computer network 2008. In some implementations, the resource manager 2006 may facilitate the provision of computing resources by one or more resource providers 2002 to one or more computing devices 2004. The resource manager 2006 may receive a request for a computing resource from a particular computing device 2004. The resource manager 2006 may identify one or more resource providers 2002 capable of providing the computing resource requested by the computing device 2004. The resource manager 2006 may select a resource provider 2002 to provide the computing resource. The resource manager 2006 may facilitate a connection between the resource provider 2002 and a particular computing device 2004. In some implementations, the resource manager 2006 may establish a connection between a particular resource provider 2002 and a particular computing device 2004. In some implementations, the resource manager 2006 may redirect a particular computing device 2004 to a particular resource provider 2002 with the requested computing resource.

Figure 21:
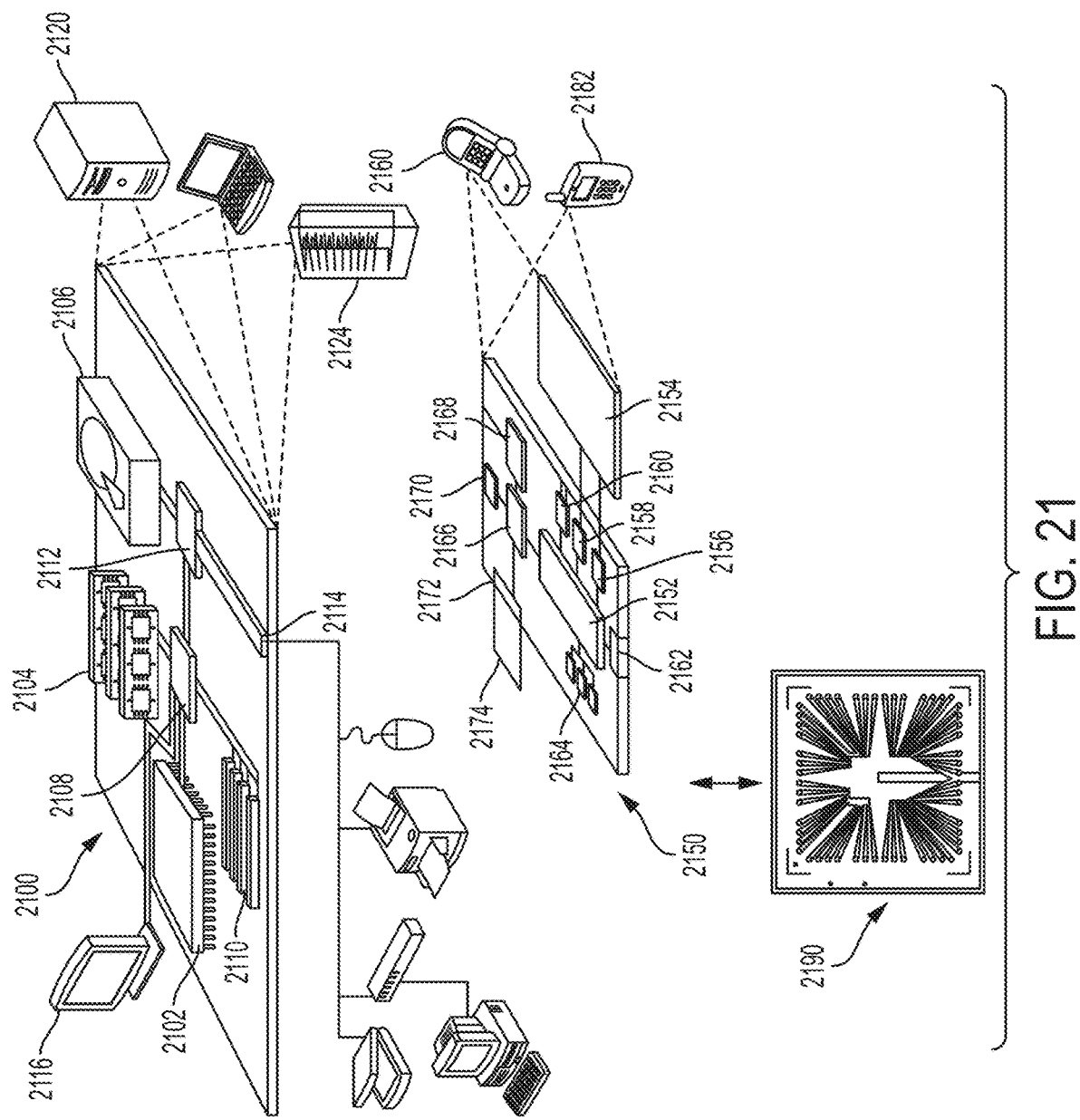
FIG. 21 is a block diagram of an example computing device and an example mobile computing device, used in certain embodiments of the biofluid collection and sensing device described herein.

FIG. 21 shows an example of a computing device 2100 and a mobile computing device 2150 that can be used with biofluid collection sensing device 2190 in the embodiments described in this disclosure. The computing device 2100 is intended to represent various forms of digital computers, such as laptops, desktops, workstations, personal digital assistants, servers, blade servers, mainframes, and other appropriate computers. The mobile computing device 2150 is intended to represent various forms of mobile devices, such as personal digital assistants, cellular telephones, smart-phones, and other similar computing devices. The components shown here, their connections and relationships, and their functions, are meant to be examples only, and are not meant to be limiting. For example, the biofluid collection and sensing device can transmit biomarker data to various embodiments of the computing device 2100 and mobile computing device 2150 described herein.

The computing device 2100 includes a processor 2102, a memory 2104, a storage device 2106, a high-speed interface 2108 connecting to the memory 2104 and multiple high-speed expansion ports 2110, and a low-speed interface 2112 connecting to a low-speed expansion port 2114 and the storage device 2106. Each of the processor 2102, the memory 2104, the storage device 2106, the high-speed interface 2108, the high-speed expansion ports 2110, and the low-speed interface 2112, are interconnected using various busses, and may be mounted on a common motherboard or in other manners as appropriate. The processor 2102 can process instructions for execution within the computing device 2100, including instructions stored in the memory 2104 or on the storage device 2106 to display graphical information for a GUI on an external input/output device, such as a display 2116 coupled to the high-speed interface 2108. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system). Thus, as the term is used herein, where a plurality of functions are described as being performed by "a processor", this encompasses embodiments wherein the plurality of functions are performed by any number of processors (one or more) of any number of computing devices (one or more). Furthermore, where a function is described as being performed by "a processor", this encompasses embodiments wherein the function is performed by any number of processors (one or more) of any number of computing devices (one or more) (e.g., in a distributed computing system).

The memory 2104 stores information within the computing device 2100. In some implementations, the memory 2104 is a volatile memory unit or units. In some implementations, the memory 2104 is a non-volatile memory unit or units. The memory 2104 may also be another form of computer-readable medium, such as a magnetic or optical disk.

The storage device 2106 is capable of providing mass storage for the computing device 2100. In some implementations, the storage device 2106 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 2102), perform one or more methods, such as those described above. The instructions can also be stored by one or more storage devices such as computer- or machine-readable mediums (for example, the memory 2104, the storage device 2106, or memory on the processor 2102).

The high-speed interface 2108 manages bandwidth-intensive operations for the computing device 2100, while the low-speed interface 2112 manages lower bandwidth-intensive operations. Such allocation of functions is an example only. In some implementations, the high-speed interface 2108 is coupled to the memory 2104, the display 2116 (e.g., through a graphics processor or accelerator), and to the high-speed expansion ports 2110, which may accept various expansion cards (not shown). In the implementation, the low-speed interface 2112 is coupled to the storage device 2106 and the low-speed expansion port 2114. The low-speed expansion port 2114, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 2100 may be implemented in a number of different forms, as shown in the figure. For example, it may be implemented as a standard server 2120, or multiple times in a group of such servers. In addition, it may be implemented in a personal computer such as a laptop computer 2122. It may also be implemented as part of a rack server system 2124. Alternatively, components from the computing device 2100 may be combined with other components in a mobile device (not shown), such as a mobile computing device 2150. Each of such devices may contain one or more of the computing device 2100 and the mobile computing device 2150, and an entire system may be made up of multiple computing devices communicating with each other.

The mobile computing device 2150 includes a processor 2152, a memory 2164, an input/output device such as a display 2154, a communication interface 2166, and a transceiver 2168, among other components. The mobile computing device 2150 may also be provided with a storage device, such as a micro-drive or other device, to provide additional storage. Each of the processor 2152, the memory 2164, the display 2154, the communication interface 2166, and the transceiver 2168, are interconnected using various buses, and several of the components may be mounted on a common motherboard or in other manners as appropriate.

The processor 2152 can execute instructions within the mobile computing device 2150, including instructions stored in the memory 2164. The processor 2152 may be implemented as a chipset of chips that include separate and multiple analog and digital processors. The processor 2152 may provide, for example, for coordination of the other components of the mobile computing device 2150, such as control of user interfaces, applications run by the mobile computing device 2150, and wireless communication by the mobile computing device 2150.

The processor 2152 may communicate with a user through a control interface 2158 and a display interface 2156 coupled to the display 2154. The display 2154 may be, for example, a TFT (Thin-Film-Transistor Liquid Crystal Display) display or an OLED (Organic Light Emitting Diode) display, or other appropriate display technology. The display interface 2156 may comprise appropriate circuitry for driving the display 2154 to present graphical and other information to a user. The control interface 2158 may receive commands from a user and convert them for submission to the processor 2152. In addition, an external interface 2162 may provide communication with the processor 2152, so as to enable near area communication of the mobile computing device 2150 with other devices. The external interface 2162 may provide, for example, for wired communication in some implementations, or for wireless communication in other implementations, and multiple interfaces may also be used.

The memory 2164 stores information within the mobile computing device 2150. The memory 2164 can be implemented as one or more of a computer-readable medium or media, a volatile memory unit or units, or a non-volatile memory unit or units. An expansion memory 2174 may also be provided and connected to the mobile computing device 2150 through an expansion interface 2172, which may include, for example, a SIMM (Single In Line Memory Module) card interface. The expansion memory 2174 may provide extra storage space for the mobile computing device 2150, or may also store applications or other information for the mobile computing device 2150. Specifically, the expansion memory 2174 may include instructions to carry out or supplement the processes described above, and may include secure information also. Thus, for example, the expansion memory 2174 may be provide as a security module for the mobile computing device 2150, and may be programmed with instructions that permit secure use of the mobile computing device 2150. In addition, secure applications may be provided via the SIMM cards, along with additional information, such as placing identifying information on the SIMM card in a non-hackable manner.

The memory may include, for example, flash memory and/or NVRAM memory (nonvolatile random access memory), as discussed below. In some implementations, instructions are stored in an information carrier such that the instructions, when executed by one or more processing devices (for example, processor 2152), perform one or more methods, such as those described above. The instructions can also be stored by one or more storage devices, such as one or more computer- or machine-readable mediums (for example, the memory 2164, the expansion memory 2174, or memory on the processor 2152). In some implementations, the instructions can be received in a propagated signal, for example, over the transceiver 2168 or the external interface 2162.

The mobile computing device 2150 may communicate wirelessly through the communication interface 2166, which may include digital signal processing circuitry where necessary. The communication interface 2166 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 2168 using a radio-frequency. In addition, short-range communication may occur, such as using a Bluetooth®, Wi-Fi™, or other such transceiver (not shown). In addition, a GPS (Global Positioning System) receiver module 2170 may provide additional navigation- and location-related wireless data to the mobile computing device 2150, which may be used as appropriate by applications running on the mobile computing device 2150.

Embodiments of the sensing device described herein may comprise electronic circuitry for local electronic processing of detected and/or produced electrical signals, and/or the sensing device may be designed for operation with a processor of a separate component (e.g., a wearable apparatus in which the sensing device is a plug-in or fixed module), and/or for transmission of signals and/or data to an external processor (e.g., via the wireless means described above). The sensing device and/or wearable apparatus may comprise an energy source (e.g., battery).

The mobile computing device 2150 may also communicate audibly using an audio codec 2160, which may receive spoken information from a user and convert it to usable digital information. The audio codec 2160 may likewise generate audible sound for a user, such as through a speaker, e.g., in a handset of the mobile computing device 2150. Such sound may include sound from voice telephone calls, may include recorded sound (e.g., voice messages, music files, etc.) and may also include sound generated by applications operating on the mobile computing device 2150.

The mobile computing device 2150 may be implemented in a number of different forms, as shown in the figure. For example, it may be implemented as a cellular telephone 2180. It may also be implemented as part of a smart-phone 2182, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

Elements of different implementations described herein may be combined to form other implementations not specifically set forth above. Elements may be left out of the processes, computer programs, databases, etc. described herein without adversely affecting their operation. In addition, the logic flows depicted in the figures do not require the particular order shown, or sequential order, to achieve desirable results. Various separate elements may be combined into one or more individual elements to perform the functions described herein. In view of the structure, functions and apparatus of the systems and methods described here, in some implementations.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A wearable biofluid collection and sensing device, the device comprising:
    an interface and/or interface surface comprising at least one biocompatible material for directly contacting a body part;
    at least one inlet disposed at the interface and/or interface surface for receiving a biofluid from the body part;
    at least one outlet for evacuating the biofluid;
    a plurality of semiconductor sensors for detecting one or more biomarkers in the received biofluid;
    at least one microfluidic and/or nanofluidic channel that is in fluid communication with the at least one inlet, the plurality of semiconductor sensors, and the at least one outlet; and
    at least one zero-energy micro pump disposed after the at least one inlet along a direction of flow of the biofluid through the wearable biofluid collection and sensing device, the at least one zero-energy micro pump for controlling the flow of the biofluid through the at least one microfluidic and/or nanofluidic channel from the at least one inlet to the plurality of semiconductor sensors.

2. The biofluid collection and sensing device of claim 1, further comprising at least one reference electrode for biasing a gate of at least one of the plurality of semiconductor sensors.

3. The biofluid collection and sensing device of claim 1, wherein the one or more biomarkers include one or more members selected from the group consisting of ions, hormones, steroids, metabolites, and organic compounds.

4. The biofluid collection and sensing device of claim 1, wherein the plurality of semiconductor sensors comprise one or more arrays of field effect transistors (FETs).

5. The biofluid collection and sensing device of claim 4, wherein the one or more arrays of field effect transistors (FETs) comprise at least one fully depleted FET (FD-FET).

6. The biofluid collection and sensing device of claim 1, wherein the plurality of semiconductor sensors comprise functionalized gates, wherein the functionalized gates comprise at least one member selected from the group consisting of a selective moiety, aptamers, antibodies, and enzymes for the selective detection of a biomarker of interest.

7. The biofluid collection and sensing device of claim 1, wherein the at least one microfluidic and/or nanofluidic channel is shaped and sized to transfer the bio-fluid from the at least one inlet, through the at least one microfluidic and/or nanofluidic channel, and out of the at least one outlet via capillary motion.

8. The biofluid collection and sensing device of claim 1, the at least one zero-energy micro pump comprises a plurality of micro-pillars.

9. The biofluid collection and sensing device of claim 1, further comprising (i) a flow rate sensor for measuring a flow rate of the biofluid through the at least one microfluidic and/or nanofluidic channel, (ii) a sweat rate sensor for measuring a rate at which the biofluid is received from and/or is emanated from a user of the wearable biofluid collection and sensing device, or both of (i) and (ii).

10. The biofluid collection and sensing device of claim 1, further comprising a temperature sensor for measuring one or more members selected from the group consisting of a temperature of the body part to which the wearable biofluid collection and sensing device is in physical contact, a temperature of the biofluid, and a temperature of a surrounding environment.

11. The biofluid collection and sensing device of claim 1, further comprising a conductivity sensor for measuring a conductivity of the received biofluid.

12. The biofluid collection and sensing device of claim 1, further comprising an electronic circuit operably connected to the plurality of semiconductor sensors, wherein the electronic circuit operates the plurality of semiconductor sensors and/or produces and/or transmits signals representative of measured data from the plurality of semiconductor sensors corresponding to a presence and/or amount of the one or more biomarkers.

13. The biofluid collection and sensing device of claim 12, wherein the electronic circuit is configured to detect in real-time the presence and/or concentration of at least one of the one or more biomarkers in the biofluid by determination of a change in the electrical conductivity of at least one semiconductor sensor.

14. The biofluid collection and sensing device of claim 12, wherein the electronic circuit includes analog readout circuitry and/or analog-to-digital converters comprising metal-gate FET devices fabricated in the same circuit substrate as the semiconductor sensors.

15. The biofluid collection and sensing device of claim 12, wherein the electronic circuit is configured to detect the presence and/or concentration of a plurality of different biomarkers in the biofluid by the determination of a differential signal, wherein the differential signal is derived from a control signal from a control sensor of the plurality of semiconductor sensors and a biomarker-specific signal from a functionalized sensor of the plurality of semiconductor sensors.

16. The biofluid collection and sensing device of claim 1, comprising a wireless communication element for transmitting data and/or signals measured and/or calculated by the wearable biofluid collection and sensing device to an external device.

17. The biofluid collection and sensing device of claim 1, wherein at least one of the plurality of semiconductor sensors is a potassium sensor comprising an FD-FET sensor and one of (i) and (ii) as follows: (i) an 18-crown ether and (ii) an ion selective membrane.

18. The biofluid collection and sensing device of one of claim 1, wherein at least one of the plurality of semiconductor sensors is a sodium sensor comprising an FD-FET sensor and one of (i) and (ii) as follows: (i) a 15-crown ether and (ii) an ion selective membrane.

19. The biofluid collection and sensing device of claim 1, comprising a fixture module for disposing the wearable biofluid collection and sensing device on the body part.

20. The biofluid collection and sensing device of claim 1, wherein the interface and/or interface surface has an external surface area in a range from about 1 $mm^2$ to about 40 $cm^2$.

21. The biofluid collection and sensing device of claim 1, wherein the wearable biofluid collection and sensing device has a weight in a range from about 125 milligrams to about 1 gram.

22. A wearable apparatus comprising a biofluid collection and sensing device and a fixture module for disposing the device on a body part, wherein the biofluid collection and sensing device comprises:
    an interface and/or interface surface comprising at least one biocompatible material for directly contacting a body part;
    at least one inlet disposed at the interface and/or interface surface for receiving a biofluid from the body part;
    at least one outlet for evacuating the biofluid;
    a plurality of semiconductor sensors for detecting one or more biomarkers in the received biofluid;
    at least one microfluidic and/or nanofluidic channel that is in fluid communication with the at least one inlet, the plurality of semiconductor sensors, and the at least one outlet; and
    at least one zero-energy micro pump disposed after the at least one inlet along a direction of flow of the biofluid through the biofluid collection and sensing device, the at least one zero-energy micro pump for controlling the flow of the biofluid through the at least one microfluidic and/or nanofluidic channel from the at least one inlet to the plurality of semiconductor sensors.

23. The wearable apparatus of claim 22, wherein the fixture module comprises a skin patch.

24. A method of using a biofluid collection and sensing device, the method comprising affixing the biofluid collection and sensing device to a human body, wherein the biofluid collection and sensing device comprises:
    an interface and/or interface surface comprising at least one biocompatible material for directly contacting a body part, wherein the interface and/or the interface surface of the biofluid collection and sensing device is in contact with a surface of the human body;
    at least one inlet disposed at the interface and/or interface surface for receiving a biofluid from the body part;
    at least one outlet for evacuating the biofluid;
    a plurality of semiconductor sensors for detecting one or more biomarkers in the received biofluid;

at least one microfluidic and/or nanofluidic channel that is in fluid communication with the at least one inlet, the plurality of semiconductor sensors, and the at least one outlet; and at least one zero-energy micro pump disposed after the at least one inlet along a direction of flow of the biofluid through the biofluid collection and sensing device, the at least one zero-energy micro pump for controlling the flow of the biofluid through the at least one microfluidic and/or nanofluidic channel from the at least one inlet to the plurality of semiconductor sensors.

25. The method of claim 24, further comprising tagging the biofluid collection and sensing device with a mobile device to trigger the biofluid collection and sensing device to: (i) begin collection and sensing and/or (ii) initiate signal transmission from the biofluid collection and sensing device to the mobile device.

\* \* \* \* \*